United States Patent
Braun et al.

(10) Patent No.: US 6,564,153 B2
(45) Date of Patent: *May 13, 2003

(54) METHOD AND APPARATUS FOR PREDICTING THE PRESENCE OF AN ABNORMAL LEVEL OF ONE OR MORE PROTEINS IN THE CLOTTING CASCADE

(75) Inventors: Paul Braun, Durham, NC (US); Thomas B. Givens, Rougemont, NC (US); Timothy J. Fischer, Oro Valley, AZ (US)

(73) Assignee: bioMerieux, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/850,255

(22) Filed: May 7, 2001

(65) Prior Publication Data

US 2002/0019706 A1 Feb. 14, 2002

Related U.S. Application Data

(63) Continuation of application No. 09/001,647, filed on Dec. 31, 1997, now Pat. No. 6,321,164, which is a continuation-in-part of application No. 08/859,773, filed on May 21, 1997, now Pat. No. 6,101,449, which is a continuation of application No. 08/477,839, filed on Jun. 7, 1995, now Pat. No. 5,708,591.

(51) Int. Cl.⁷ .............................................. G01N 21/00
(52) U.S. Cl. ............................. 702/22; 702/30; 702/32; 702/19; 436/69
(58) Field of Search ......................... 702/22, 23, 27–32, 702/128, 131, 139, 179–181, 183, FOR 115–FOR 119, FOR 131, FOR 170, FOR 171, 19, 21; 700/266, 268; 73/64, 43; 703/6, 9, 11, 12; 436/69, 66, 43, 47–50, 54, 55, 174, 164, 171, 180, 805; 422/73, 68.1, 50, 61–67, 82.05; 382/133, 134, 156–159; 356/39, 42, 40; 706/924, 21, 20; 435/13; 377/10, 11

(56) References Cited

U.S. PATENT DOCUMENTS

| | | | |
|---|---|---|---|
| 3,307,392 A | 3/1967 | Owen et al. | 73/64.1 |
| 3,458,287 A | 7/1969 | Gross et al. | 23/230 |
| 3,658,480 A | 4/1972 | Kane et al. | 23/230 B |
| 4,040,788 A | 8/1977 | Simons et al. | 436/34 |
| 4,047,890 A | 9/1977 | Eichelberger et al. | 23/230 B |
| 4,199,748 A | 4/1980 | Bacus | 340/146.3 CA |
| 4,217,107 A | 8/1980 | Saito et al. | 23/230 B |
| 4,279,616 A | 7/1981 | Saito et al. | 23/230 B |
| 4,289,498 A | 9/1981 | Baughman et al. | 23/230 B |
| 4,766,083 A | 8/1988 | Miyashita et al. | 436/517 |
| 4,782,014 A | 11/1988 | Serban et al. | 435/7 |

(List continued on next page.)

FOREIGN PATENT DOCUMENTS

| | | | |
|---|---|---|---|
| DE | 2635081 | 2/1978 | G01N/33/16 |
| DE | 3502 878 | 1/1983 | C12Q/1/56 |
| EP | 0 115 459 | 8/1984 | G01N/33/68 |

(List continued on next page.)

*Primary Examiner*—Hal Wachsman
(74) *Attorney, Agent, or Firm*—Myers Bigel Sibley & Sajovec

(57) ABSTRACT

A method is disclosed for predicting the presence of an abnormal level of one or more proteins in the clotting cascade from at least one time-dependent measurement profile. At least one time-dependent measurement on an unknown sample is performed and a respective property of said sample is measured over time so as to derive a time-dependent measurement profile. A set of a plurality of predictor variables are defined which sufficiently define the data of the time-dependent measurement profile. A model is then derived that represents the relationship between the abnormality and the set of predictor variables. Subsequently, the model is utilized to predict which protein or proteins in the clotting cascade are at an abnormal level, with the prediction being a more informative prediction than clot time alone.

4 Claims, 29 Drawing Sheets

U.S. PATENT DOCUMENTS

| | | | |
|---|---|---|---|
| 4,902,630 A | 2/1990 | Bennett et al. | 436/546 |
| 4,965,725 A | 10/1990 | Rutenberg | 364/413.1 |
| 4,998,535 A | 3/1991 | Selker et al. | 128/696 |
| 5,003,065 A | 3/1991 | Merritt et al. | 540/469 |
| 5,055,412 A | 10/1991 | Proksch | 436/69 |
| 5,156,974 A | 10/1992 | Grossman et al. | 436/69 |
| 5,169,786 A * | 12/1992 | Carroll et al. | 436/69 |
| 5,218,529 A | 6/1993 | Meyer et al. | 364/413.01 |
| 5,221,628 A | 6/1993 | Anderson et al. | |
| 5,358,852 A | 10/1994 | Wu | 435/7.94 |
| 5,388,164 A | 2/1995 | Yonekawa et al. | 382/6 |
| 5,473,551 A | 12/1995 | Sato et al. | 364/496 |
| 5,473,732 A | 12/1995 | Chang | 395/77 |
| 5,500,345 A | 3/1996 | Soe et al. | 435/7.1 |
| 5,525,477 A | 6/1996 | Hassouna | 436/69 |
| 5,526,111 A | 6/1996 | Collins et al. | 73/64.43 |
| 5,553,616 A | 9/1996 | Ham et al. | 128/633 |
| 5,563,983 A | 10/1996 | Nozaki et al. | 395/23 |
| 5,567,596 A * | 10/1996 | Diamond et al. | 435/13 |
| 5,591,403 A | 1/1997 | Gavin et al. | 422/73 |
| 5,593,897 A | 1/1997 | Potempa et al. | 436/507 |
| 5,646,046 A * | 7/1997 | Fischer et al. | 436/43 |
| 5,670,329 A | 9/1997 | Oberhardt | 435/13 |
| 5,705,395 A | 1/1998 | Griffin et al. | 436/69 |
| 5,708,591 A | 1/1998 | Givens et al. | 364/497 |
| 5,715,821 A | 2/1998 | Faupel | 1286/653.1 |
| 5,716,795 A | 2/1998 | Matschiner | 435/13 |
| 5,834,223 A | 11/1998 | Griffin et al. | 435/13 |
| 5,856,114 A | 1/1999 | Mann et al. | 436/13 |
| 5,862,304 A | 1/1999 | Ravdin et al. | 395/22 |
| 5,981,285 A * | 11/1999 | Carroll et al. | 702/23 |
| 6,010,911 A | 1/2000 | Baugh et al. | 422/73 |
| 6,040,147 A | 3/2000 | Ridker et al. | 435/7.24 |
| 6,101,449 A * | 8/2000 | Givens et al. | 702/22 |
| 6,269,313 B1 | 7/2001 | Givens et al. | 702/22 |

FOREIGN PATENT DOCUMENTS

| | | | | |
|---|---|---|---|---|
| EP | 0 434 377 | 6/1991 | | G01N/33/86 |
| EP | 0 525 273 | 2/1993 | | G01N/33/49 |
| EP | 818 680 | 1/1998 | | G01N/33/546 |
| EP | 841 566 | 5/1998 | | G01N/33/96 |
| FR | 2364 453 | 9/1976 | | G01N/33/16 |
| GB | 2005014 | 4/1979 | | G01N/33/16 |
| JP | 59-203959 | 11/1984 | | G01N/33/86 |
| JP | 60-114768 | 6/1985 | | G01N/35/02 |
| JP | 61-272655 | 12/1986 | | G01N/33/49 |
| JP | 05-180835 | 12/1991 | | G01N/33/53 |
| JP | 06-027115 | 7/1992 | | G01N/33/86 |
| JP | 04-254760 | 9/1992 | | G01N/33/53 |
| JP | 06-249855 | 9/1994 | | G01N/33/86 |
| JP | 10-104239 | 9/1996 | | G01N/33/86 |
| RU | 2012877 | 4/1991 | | G01N/33/48 |
| RU | 2061953 | 6/1996 | | G01N/33/86 |
| RU | 2070327 | 12/1996 | | G01N/33/50 |
| SU | 590665 | 2/1976 | | G01N/33/16 |
| SU | 1076086 | 2/1984 | | A61B/5/14 |
| SU | 1691741 | 8/1989 | | G01N/33/48 |
| SU | 1777089 | 6/1990 | | G01N/33/86 |
| WO | WO 86/06840 | 11/1986 | | G01N/33/86 |
| WO | WO 89/09628 | 10/1989 | | |
| WO | WO 91/00872 | 1/1991 | | C07K/15/28 |
| WO | WO 91/01383 | 2/1991 | | C12Q/1/56 |
| WO | WO 91/01497 | 2/1991 | | G01N/31/00 |
| WO | WO 91/02812 | 3/1991 | | C12Q/1/56 |
| WO | WO 91/05874 | 5/1991 | | C12Q/1/00 |
| WO | WO 91/08460 | 6/1991 | | G01N/21/00 |
| WO | WO 91/16453 | 10/1991 | | C12Q/1/56 |
| WO | WO 93/07491 | 4/1993 | | G01N/33/68 |
| WO | WO 93/09438 | 5/1993 | | G01N/33/68 |
| WO | WO 93/24530 | 12/1993 | | C07K/15/06 |
| WO | WO 94/07145 | 3/1994 | | G01N/33/86 |
| WO | WO 94/11714 | 5/1994 | | G01J/3/02 |
| WO | WO 94/16095 | 7/1994 | | C12Q/1/00 |
| WO | WO 95/05590 | 2/1995 | | G01N/1/28 |
| WO | WO 95/08121 | 3/1995 | | G01N/33/86 |
| WO | WO 96/42018 | 9/1995 | | G01N/33/86 |
| WO | WO 95/30154 | 11/1995 | | G01N/33/86 |
| WO | WO 96/06624 | 3/1996 | | A61K/35/16 |
| WO | WO 96/14581 | 5/1996 | | G01N/33/86 |
| WO | WO 96/21740 | 7/1996 | | C12Q/1/56 |
| WO | WO 96/41291 | 12/1996 | | G06F/19/00 |
| WO | WO 97/04317 | 2/1997 | | G01N/33/68 |
| WO | WO 97/20066 | 6/1997 | | C12Q/1/56 |
| WO | WO 97/34698 | 9/1997 | | B01L/3/00 |
| WO | WO 98/09628 | 3/1998 | | A61K/31/495 |
| WO | WO 99/34208 | 7/1999 | | |
| WO | WO 99/47699 | 9/1999 | | |

* cited by examiner $\eta=0.9, \alpha=0.1$

| Hidden Layer Size | Error | | $\varphi_{ODB}$ |
|---|---|---|---|
| | $E_{tr}$ | $E_{DV}$ | |
| 2 | 0.384 | 0.376 | 0.848 |
| 4 | 0.386 | 0.354 | 0.835 |
| 6 | 0.341 | 0.328 | 0.875 |
| 8 | 0.358 | 0.327 | 0.857 |
| 10 | 0.346 | 0.325 | 0.856 |
| 12 | 0.347 | 0.322 | 0.855 |

Predictor Variables

| Predictor Variable | Description |
|---|---|
| $pv_{j1} = \left(\dfrac{dT}{dt}\right)_{min}$ | minimum of the first derivative |
| $pv_{j2} = t \text{ at } \left(\dfrac{dT}{dt}\right)_{min}$ | time index of the minimum of the first derivative |
| $pv_{j3} = \left(\dfrac{d^2T}{dt^2}\right)_{min}$ | minimum of the second derivative |
| $pv_{j4} = t \text{ at } \left(\dfrac{d^2T}{dt^2}\right)_{min}$ | index of the minimum of the second derivative |
| $pv_{j5} = \left(\dfrac{d^2T}{dt^2}\right)_{max}$ | maximum of the second derivative |
| $pv_{j6} = t \text{ at } \left(\dfrac{d^2T}{dt^2}\right)_{max}$ | index of the maximum of the second derivative |
| $pv_{j7} = T_{t_0} - T_{t_R}$ | overall change in transmittence during the reaction |

| Condition | Training Set | | Cross-Validation Set | |
|---|---|---|---|---|
| | Negative | Positive | Negative | Positive |
| FII < 30% | 346 | 32 | 362 | 19 |
| FV < 30% | 362 | 12 | 366 | 12 |
| FVII < 30% | 354 | 32 | 343 | 35 |
| FVIII < 30% | 342 | 32 | 367 | 19 |
| FIX < 30% | 344 | 26 | 360 | 15 |
| FX < 30% | 294 | 76 | 324 | 58 |
| FX < 10% | 338 | 32 | 369 | 13 |
| FX < 50% | 266 | 104 | 289 | 93 |
| FXI < 30% | 358 | 12 | 367 | 12 |
| FXII < 30% | 346 | 32 | 362 | 24 |

| Condition | | APTT-PT NN | | APPTT NN | | PT NN | | APTT CT | | PT CT | | Comments |
|---|---|---|---|---|---|---|---|---|---|---|---|---|
| Factor | Cut-off | Area | SE | Area | SE | Area | SE | Area | SE | Area | SE | |
| FII | 30% | 0.999 | 0.001 | 0.998 | 0.002 | 0.876 | 0.032 | 0.594 | 0.044 | 0.922 | 0.016 | Best results for APTT NN, APTT-PT NN |
| FV | 30% | 0.787 | 0.087 | 0.942 | 0.018 | 0.760 | 0.090 | 0.412 | 0.076 | 0.815 | 0.026 | Best results for APTT NN |
| FVII | 30% | 0.791 | 0.045 | 0.724 | 0.049 | 0.728 | 0.041 | 0.661 | 0.036 | 0.882 | 0.017 | NNs do not provide either greater area under curve or higher specificity (Fig. 5) |
| FVIII | 30% | 0.826 | 0.065 | 0.794 | 0.060 | 0.752 | 0.055 | 0.789 | 0.027 | 0.423 | 0.082 | NNs do not give greater area under curve; do tend toward higher specificity (Fig. 6) |
| FIX | 30% | 0.691 | 0.087 | 0.634 | 0.090 | 0.961 | 0.011 | 0.622 | 0.090 | 0.738 | 0.073 | Best results for PT NN |
| FX | 30% | 0.827 | 0.041 | 0.809 | 0.043 | 0.830 | 0.025 | 0.579 | 0.034 | 0.894 | 0.016 | NNs do not give greater area under curve; do tend toward higher specificity (Fig. 11) |
| FXI | 30% | 0.790 | 0.093 | 0.692 | 0.080 | 0.826 | 0.033 | 0.509 | 0.091 | 0.675 | 0.077 | Best results for APTT-PT NN if greater specificity is desired (Fig. 8) |
| FXII | 30% | 0.902 | 0.039 | 0.710 | 0.055 | 0.586 | 0.067 | 0.659 | 0.070 | 0.530 | 0.058 | Best results for APTT-PT NN |

FIG. 23

| Condition | | APTT-PT NN | | PT CT | |
|---|---|---|---|---|---|
| Factor | Cut-off | Area | SE | Area | SE |
| FX | < 10% | 0.994 | 0.004 | 0.951 | 0.016 |
| FX | < 30% | 0.827 | 0.041 | 0.894 | 0.016 |
| FX | < 50% | 0.748 | 0.035 | 0.900 | 0.016 |

FIG. 24

| Factor | APTT-PT NN | | | APTT Clot Time | PT Clot Time |
|---|---|---|---|---|---|
| | Slope | Intercept | r | r | r |
| FII | 0.53 | 46.7 | 0.62 | 0.05 | 0.05 |
| FV | 0.31 | 64.2 | 0.45 | 0.07 | 0.01 |
| FVII | 0.18 | 8.5 | 0.32 | 0.17 | 0.08 |
| FVIII | -0.14 | 140.5 | 0.02 | 0.15 | 0.13 |
| FIX | 0.38 | 60.7 | 0.54 | 0.26 | 0.15 |
| FX | 0.50 | 53.2 | 0.60 | 0.11 | 0.13 |
| FXI | 0.20 | 75.4 | 0.37 | 0.27 | 0.08 |
| FXII | 0.35 | 54.8 | 0.51 | 0.10 | 0.08 |
| Fibrinogen | 0.89 | 61.9 | 0.97 | 0.07 | 0.07 |

FIG. 25

| Deficiency or Condition | APTT | | | | | PT | | | | |
|---|---|---|---|---|---|---|---|---|---|---|
| | Sensitivity | Specificity | PPV | NPV | Efficiency | Sensitivity | Specificity | PPV | NPV | Efficiency |
| FII < 30% | 0.84 | 0.93 | 0.39 | 0.99 | 0.93 | 0.79 | 0.96 | 0.51 | 0.99 | 0.95 |
| FV < 30% | 0.00 | 0.98 | 0.00 | 0.97 | 0.95 | 0.00 | 0.99 | 0.00 | 0.97 | 0.96 |
| FVII < 30% | 0.22 | 0.97 | 0.42 | 0.92 | 0.90 | 0.03 | 0.97 | 0.09 | 0.91 | 0.88 |
| FVIII < 30% | 0.33 | 0.96 | 0.21 | 0.98 | 0.94 | 0.00 | 0.96 | 0.00 | 0.97 | 0.93 |
| FIX < 30% | 0.47 | 0.91 | 0.18 | 0.98 | 0.89 | 0.00 | 0.96 | 0.00 | 0.96 | 0.92 |
| FX < 30% | 0.62 | 0.85 | 0.43 | 0.93 | 0.82 | 0.66 | 0.86 | 0.46 | 0.93 | 0.83 |
| FXI < 30% | 0.67 | 0.96 | 0.35 | 0.99 | 0.95 | 1.00 | 0.96 | 0.45 | 1.00 | 0.96 |
| FXII < 30% | 0.79 | 0.90 | 0.34 | 0.98 | 0.89 | 0.50 | 0.92 | 0.29 | 0.97 | 0.89 |
| Heparin < 0.051 U/ml | 0.76 | 0.86 | 0.72 | 0.88 | 0.83 | 0.77 | 0.74 | 0.59 | 0.87 | 0.75 |

FIG. 30

METHOD AND APPARATUS FOR PREDICTING THE PRESENCE OF AN ABNORMAL LEVEL OF ONE OR MORE PROTEINS IN THE CLOTTING CASCADE

This application is a continuation of commonly owned, U.S. application Ser. No. 09/001,647 entitled A Method and Apparatus for Predicting the Presence of an Abnormal Level of One or More Proteins in the Clotting Cascade, filed on Dec. 31, 1997 (now U.S. Pat. No. 6,321,164), which is a continuation-in-pan of U.S. application Ser. No. 08/859,773 to Givens, et al. (now U.S. Pat. No. 6,101,449), filed May 21, 1997, which is a continuation of U.S. application Ser. No. 08/477,839 to (livens, et al. (now U.S. Pat. No. 5,708,591), filed Jun. 7, 1995, the disclosures of which are hereby incorporated herein in its entirety by reference. This application is further related to the following publications, the subject matter of each also being incorporated herein by reference:

1. B. Pohl, C. Beringer, M. Bomhard, F. Keller, The quick machine—a mathematical model for the extrinsic activation of coagulation, *Haemostasis,* 24, 325–337 (1994).
2. J. Brandt, D. Triplett, W. Rock, E. Bovill, C. Arkin, Effect of lupus anticoagulants on the activated partial thromboplastin time, *Arch Pathol Lab Med,* 115, 109–14 (1991).
3. I. Talstad, Which coagulation factors interfere with the one-stage prothrombin time?, *Haemostasis,* 23, 19–25 (1993).
4. P. Baumann, T. Jurgensen, C. Heuck, Computerized analysis of the in vitro activation of the plasmatic clotting system, *Haemostasis,* 19, 309–321 (1989).
5. C. Heuck, P. Baumann, Kinetic analysis of the clotting system in the presence of heparin and depolymerized heparin, *Haemostasis,* 21, 10–18 (1991).
6. M. Astion and P. Wilding, The application of backpropagation neural networks to problems in pathology and laboratory medicine, *Arch Pathol Lab Med,* 116, 995–1001 (1992).
7. M. Astion, M. Wener, R. Thomas, G. Hunder, and D. Bloch, Overtraining in neural networks that interpret clinical data, *Clinical Chemistry,* 39, 1998–2004 (1993).
8. J. Furlong, M. Dupuy, and J. Heinsimer, Neural network analysis of serial cardiac enzyme data, *A.J.C.P.,* 96, 134–141 (1991).
9. W. Dassen, R. Mulleneers, J. Smeets, K. den Dulk, F. Cruz, P. Brugada, and H. Wellens, Self-learning neural networks in electrocardiography, *J. Electrocardiol,* 23, 200–202 (1990).
10. E. Baum and D. Haussler, What size net gives valid generalization? *Advances in Neural Information Processing Systems,* Morgan Kauffman Publishers, San Mateo, Calif., 81–90 (1989).
11. A. Blum, *Neural Networks in C++,* John Wiley & Sons, New York, (1992).
12. S. Haykin, *Neural Networks A Comprehensive Foundation,* Macmillan College Publishing Company, New York, (1994).
13. J. Swets, Measuring the accuracy of diagnostic systems, *Science,* 240, 1285–1293 (1988).
14. M. Zweig and G. Campbell, Receiver-operating characteristic (ROC) plots: a fundamental evaluation tool in clinical medicine, *Clinical Chemistry,* 39, 561–577 (1993).
15. D. Bluestein, L. Archer, The sensitivity, specificity and predictive value of diagnostic information: a guide for clinicians, *Nurse Practitioner,* 16, 39–45 (1991).
16. C. Schweiger, G. Soeregi, S. Spitzauer, G. Maenner, and A. Pohl, Evaluation of laboratory data by conventional statistics and by three types of neural networks, *Clinical Chemistry,* 39, 1966–1971 (1993).

BACKGROUND OF THE INVENTION

Blood clots are the end product of a complex chain reaction where proteins form an enzyme cascade acting as a biologic amplification system. This system enables relatively few molecules of initiator products to induce sequential activation of a series of inactive proteins, known as factors, culminating in the production of the fibrin clot. Mathematical models of the kinetics of the cascade's pathways have been previously proposed.

In Porn et al. (1994), supra, a dynamic model of the extrinsic coagulation cascade was described where data were collected for 20 samples using quick percent, activated partial thromboplastin time (APTT), throinbin time (TT), fibrinogen, factor (F) II, FV, FVII, FX, anti-thrombin III (ATIII), and factor degradation product (FDP) assays. These data were used as input to the model and the predictive output compared to actual recovered prothrombin time (PT) screening assay results. The model accurately predicted the PT result in only 11 of 20 cases. These coagulation cascade models demonstrate: (1) the complexity of the clot formation process, and (2) the difficulty in associating PT clot times alone with specific conditions.

Thrombosis and hemostasis testing is the in vitro study of the ability of blood to form clots and to break clots in vivo. Coagulation (hemostasis) assays began as manual methods where clot formation was observed in a test tube either by tilting the tube or removing fibrin strands by a wire loop. The goal was to determine if a patient's blood sample would clot after certain materials were added. It was later determined that the amount of time from initiation of the reaction to the point of clot formation in vitro is related to congenital disorders, acquired disorders, and therapeutic monitoring. In order to remove the inherent variability associated with the subjective endpoint determinations of manual techniques, instrumentation has been developed to measure clot time, based on (1) electromechanical properties, (2) clot elasticity, (3) light scattering, (4) fibrin adhesion, and (5) impedance. For light scattering methods, data is gathered that represents the transmission of light through the specimen as a function of time (an optical time-dependent measurement profile).

Two assays, the Prothrombin Time (PT) and Activated Partial Thromboplastin Time (APTT), are widely used to screen for abnormalities in the coagulation system, although several other screening assays can be used, e.g. protein C, fibrinogen, protein S and/or thrombin time. If screening assays show an abnormal result, one or several additional tests are needed to isolate the exact source of the abnormality. The PT and ANT assays rely primarily upon measurement of time required for clot time, although some variations of the PT also use the amplitude of the change in optical signal in estimating fibrinogen concentration.

Blood coagulation is affected by administration of drugs, in addition to the vast array of internal factors and proteins that normally influence clot formation. For example, heparin is a widely-used therapeutic drug that is used to prevent thrombosis following surgery or under other conditions, or is used to combat existing thrombosis. The administration of heparin is typically monitored using the APTT assay, which gives a prolonged clot time in the presence of heparin. Clot times for PT assays are affected to a much smaller degree. Since a number of other plasma abnormalities may also cause prolonged APTT results, the ability to discriminate between these effectors from screening assay results may be clinically significant.

Using a sigmoidal curve fit to a profile, Baumann, et al. (1989) showed that a ratio of two coefficients was unique for a select group of blood factor deficiencies when fibrinogen was artificially maintained by addition of exogenous fibrinogen to a fixed concentration, and that same ratio also correlates heparin to FII deficiency and FXa deficiencies. However, the requirement for artificially fixed fibrinogen makes this approach inappropriate for analysis of clinical specimens. The present invention makes it possible to predict a congenital or acquired imbalance or therapeutic condition for clinical samples from a time-dependent measurement profile without artificial manipulation of samples.

The present invention was conceived of and developed for predicting the presence of congenital or acquired imbalances or therapeutic conditions of an unknown sample based on one or more time-dependent measurement profiles, such as optical time-dependent measurement profiles, where a set of predictor variables are provided which define characteristics of profile, and where in turn a model is derived that represents the relationship between a congenital or acquired imbalance or therapeutic condition and the set of predictor variables (so as to, in turn, utilize this model to predict the existence of the congenital or acquired imbalance or therapeutic condition in the unknown sample).

SUMMARY OF THE INVENTION

The present invention is directed to a method and apparatus for predicting the presence of at least one congenital or acquired imbalance or therapeutic condition from at least one time-dependent measurement profile. The method and apparatus include a) performing at least one assay on an unknown sample and measuring a respective property over time so as to derive a time-dependent measurement profile, b) defining a set of predictor variables which sufficiently define the data of the time-dependent profile, c) deriving a model that represents the relationship between a diagnostic output and the set of predictor variables, and d) utilizing the model to predict the existence of a congenital or acquired imbalance or therapeutic condition in the unknown sample relative to the diagnostic output. In one embodiment, training data is provided by performing a plurality of assays on known samples, the model is a multilayer perceptron, the relationship between the diagnostic output and the set of predictor variables is determined by at least one algorithm, and the at least one algorithm is a back propagation learning algorithm. In a second embodiment of the present invention, the relationship between the diagnostic output and the set of predictor variables is derived by a set of statistical equations.

Also in the present invention, a plurality of time-dependent measurement profiles are derived, which time-dependent measurement profiles can be optical time-dependent measurement profiles such as ones provided by a automated analyzer for thrombosis and hemostasis, where a plurality of optical measurements are taken overtime, and where the plurality of optical measurements are normalized. The optical profiles can include one or more of a PT profile, a fibrinogen profile, an APTT profile, a Thrombin Time (TT), profile, a protein C profile, a protein S profile and a plurality of other assays associated with congenital or acquired imbalances or therapeutic conditions.

BRIEF DESCRIPTION OF THE DRAWINGS

FIG. 9 is a Table comparing hidden layer size with prediction error;

FIG. 13 is a chart listing examples of predictor variables for use in the present invention;

FIG. 23 shows results of classification of coagulation factor deficiencies as determined from area under ROC curves;

FIG. 24 shows areas under ROC curves for three networks trained to classify factor deficiencies based on three different diagnostic cutoffs;

FIG. 25 shows results from linear regressions comparing factor concentrations estimated using neural network with measured factor concentrations;

FIG. 30 shows the sensitivity, specificity, efficiency and predictive value of positive test (PPV) and the predictive value of negative test (NPV), based on either APTT or PT parameters.

DESCRIPTION OF THE PREFERRED EMBODIMENTS

Figure 31:
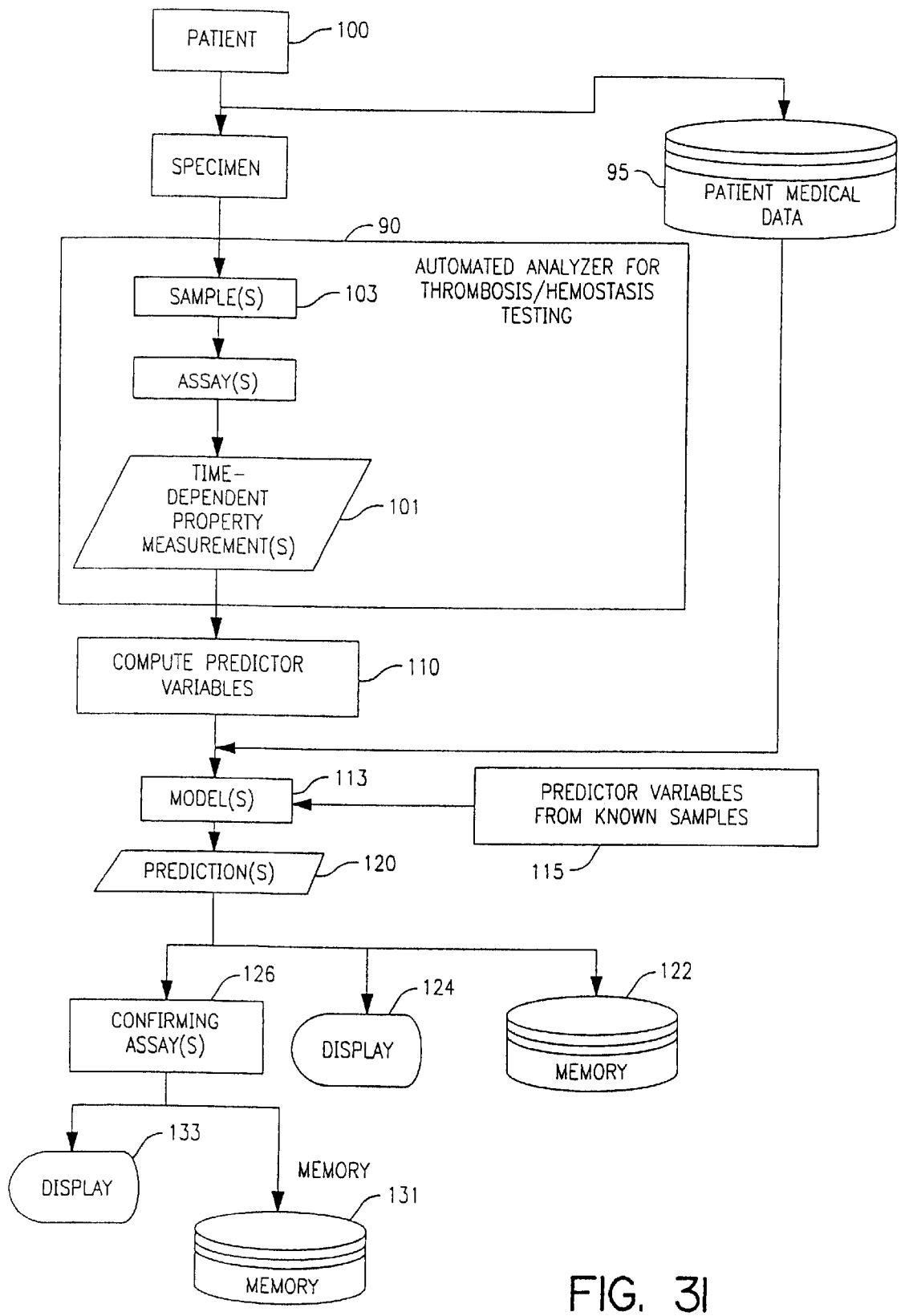
FIG. 31 is a chart illustrating embodiments of the present invention.

In the present invention, both a method and apparatus are provided for predicting the presence of at least one congenital or acquired imbalance or therapeutic condition. As can be seen in FIG. 31, one or more time-dependent measurements (101) are performed on an unknown sample (103). The term "time-dependent measurement" is referred to herein to include measurements derived from assays (e.g. PT, APTT, fibrinogen, protein C, protein S, TT, ATIII, plasminogen and factor assays). The terms "unknown sample" and "clinical sample" refer to a sample, such as one from a medical patient (100), where a congenital or acquired imbalance or therapeutic condition associated with thrombosis/hemostasis is not known (or, if suspected, has not been confirmed). In the present invention, a coagulation property is measured over time so as to derive a time-dependent measurement profile. In a preferred embodiment, the time-dependent measurement is an optical measurement for deriving an optical profile. For example, a PT profile, a fibrinogen profile, a TT profile, an APTT profile and/or variations thereof can be provided where, an unknown sample is analyzed for clot formation based on light transmittance over time through the unknown sample. In other preferred embodiment, two (or more) optical profiles are provided, such as both a PT profile and an APTT profile.

After the time-dependent measurement profiles are provided, a set of predictor variables are defined (110) which sufficiently define the data of the time-dependent profile. One or more predictor variables comprise the set. And, in one embodiment, three or more, and in a preferred embodiment, four or more predictor variables were found to desirably make up the set. It was found that the characteristics of the time-dependent measurement profile could best be defined by one or more predictor variables, including the minimum of the first derivative of the optical profile, the time index of this minimum, the maximum of the second derivative, the time index of this maximum, the overall change in transmittance during the time-dependent measurement, clotting time, slope of the optical profile prior to clot formation, and slope of the optical profile after clot formation.

After defining the set of predictor variables, a model (113) is derived which represents the relationship between a congenital or acquired imbalance or therapeutic condition and the set of predictor variables. This model can be derived from a neural network in one embodiment of the present invention. In another embodiment, the model is derived via a set of statistical equations.

Neural networks represent a branch of artificial intelligence that can be used to learn and model complex, unknown systems given some known data (115) from which it can train. Among the features of neural networks that make them an attractive alternative for modeling complex systems are:
1. They can handle noisy data well and recognize patterns even when some of the input data are obscured or missing,
2. It is unnecessary to determine what factors are relevant a priori since the network will determine during the training phase what data are relevant assuming there are at least some meaningful parameters in the set.

Figure 1:
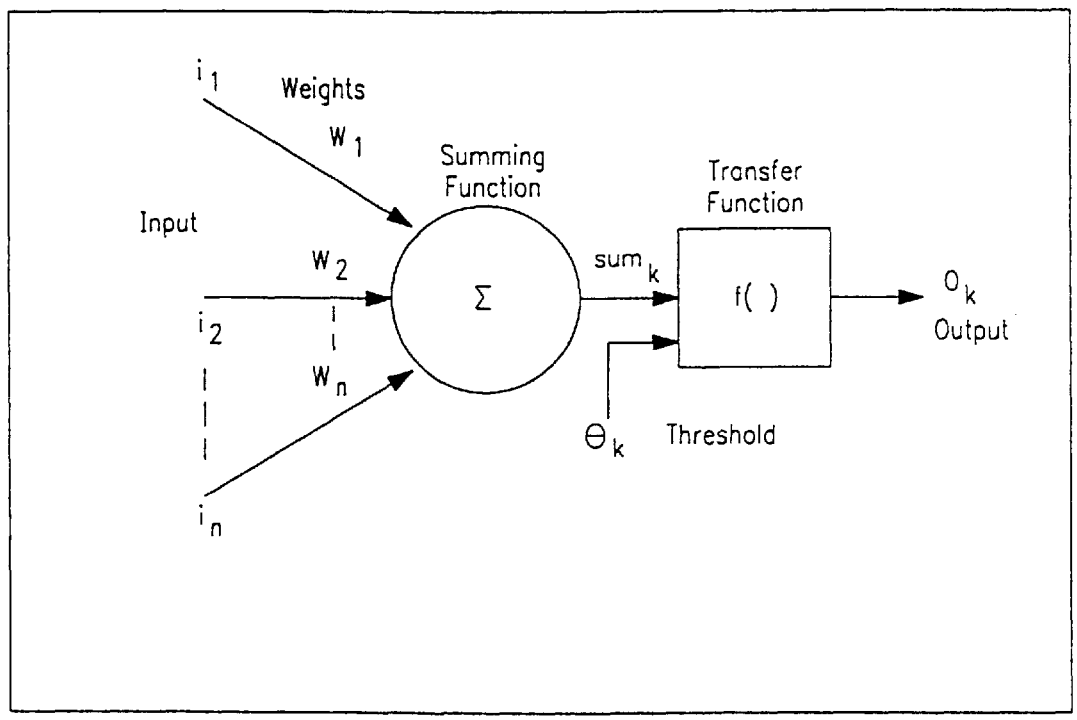
FIG. 1 is a general neuron diagram relating to the embodiment of the present invention utilizing a neural network.

Neural networks are formed from multiple layers of interconnected neurons like that shown in FIG. 1. Each neuron has one output and receives input $i_1 \ldots i_n$ from multiple other neurons over connecting links, or synapses. Each synapse is associated with a synaptic weight, $w_j$. An adder Σ or linear combiner sums the products of the input signals and synaptic weights $i_j*w_j$. The linear combiner output $sum_l$ and $\theta_l$ (a threshold which lowers or a bias which raises the output) are the input to the activation function f( ). The synaptic weights are learned by adjusting their values through a learning algorithm.

After deriving the model (113), whether based on neural networks or statistical equations, the model is utilized to predict (120) the existence of a congenital or acquired imbalance or therapeutic condition in the unknown sample relative to the time-dependent measurement profile(s). As such, a congenital or acquired imbalance or therapeutic condition can be predicted. Conditions which can be predicted as being abnormal in the present invention can include, among others, a) factor deficiencies, e.g. fibrinogen, Factors U, V, VII, VIII, IX, X, XI and XII, as well as ATIII, plasminogen, protein C, protein S. etc., b) therapeutic conditions, e.g. heparin, coumadin, etc., and c) conditions such as lupus anticoagulant, In one embodiment of the present invention, the method is performed on an automated analyzer (90). The time-dependent measurement profile, such as an optical data profile, can be provided automatically by the automated analyzer, where the unknown sample is automatically removed by an automated probe from a sample container to a test well, one or more reagents are automatically added to the test well so as to initiate the reaction within the sample. A property over tune is automatically optically monitored so as to derive the optical profile. The predicted congenital or therapeutic condition (120) can be automatically stored in a memory (122) of an automated analyzer and/or displayed (124) on the automated analyzer, such as on a computer monitor, or printed out on paper. As a further feature of the invention, if the predicted congenital or acquired imbalance or therapeutic condition is an abnormal condition, ten one or more assays for confirming the existence of the abnormal condition (126) are performed on the automated analyzer. In fact, in a preferred embodiment, the one or more confirming assays are automatically ordered and performed on the analyzer once the predicted condition is determined, with the results of the one or more confirming assays being stored in a memory (131) of the automated analyzer and/or displayed (133) on the analyzer. Also, where the unknown sample is from a medical patient, both the derived model and other patient medical data (95) can be used for predicting the imbalance/condition. If a monitoring system is used, a plurality of optical measurements at one or more wavelengths can be taken over time so as to derive the optical profile, with the optical measurements corresponding to changes in light scattering and/or light absorption in the sample. Also, the plurality of optical measurements can each be normalized to a first optical measurement. If the time-dependent measurement is an optical profile, this can be provided automatically by an analyzer, where a sample is automatically removed by an automated probe from a sample container to a test well, one or more reagents are automatically added to the test well so as to initiate the property changes within the sample, and the development of the property over time is automatically optically monitored so as to derive the optical data profile. And, the predictor variables can be a plurality of variables, three or more predictor variables, or more than three predictor variables.

EXAMPLE 1

Prediction of Heparin in Sample

This example shows a set of predictor variables that adequately describe screening assay optical profiles, develops an optimal neural network design, and determines the predictive capabilities of an abnormal condition associated with thrombosis/hemostasis (in this case for the detection of heparin) with a substantial and well-quantified test data set.

Simplastin™ L (liquid thromboplastin reagent), Platelin™ L (liquid activated partial thromboplastin time reagent), calcium chloride solution (0.025 M), imidazole buffer were obtained from Organon Tekuika Corporation, Durham, N.C., 27712, USA. All plasma specimens were collected in 3.2% or 3.8% sodium citrate in the ratio of one part anticoagulant to nine parts whole blood. The tubes were centrifuged at 2000 g for 30 minutes and then decanted into polypropylene tubes and stored at −30 until evaluated. 757 specimens were prepared from 200 samples. These specimens were tested by the following specific assays: FII, FV, FVII, FVIII, FIX, FX, FXI, FXII, heparin, fibrinogen, plasminogen, protein C, and AT-III. Samples represented normal patients, a variety of deficiencies, and therapeutic conditions. Of the specimen population 216 were positive for heparin determined by a heparin concentration greater than 0.05 units/ml measured with a chromogenic assay specific for heparin, The remaining specimens, classified as heparin-negative, included normal specimens, a variety of single or multiple factor deficiencies, and patients receiving other therapeutic drugs. Positive heparin samples ranged to 0.54 units/ml.

PT and APTT screening assays were performed on each specimen utilizing two automated analyzers (MDA™ 180s) and multiple reagent and plasma vials (Organon Teknika Corporation, Durham, N.C. 27712, USA ) over a period of five days. When clot-based coagulation assays are performed by an automated optically-based analyzer such as the MDA 180, data are collected over time that represents the normalized level of light transmission through a sample as a clot forms (the optical profile). As the fibrin clot forms, the transmission of light is decreased. The optical profile was stored from each test.

Figure 2:
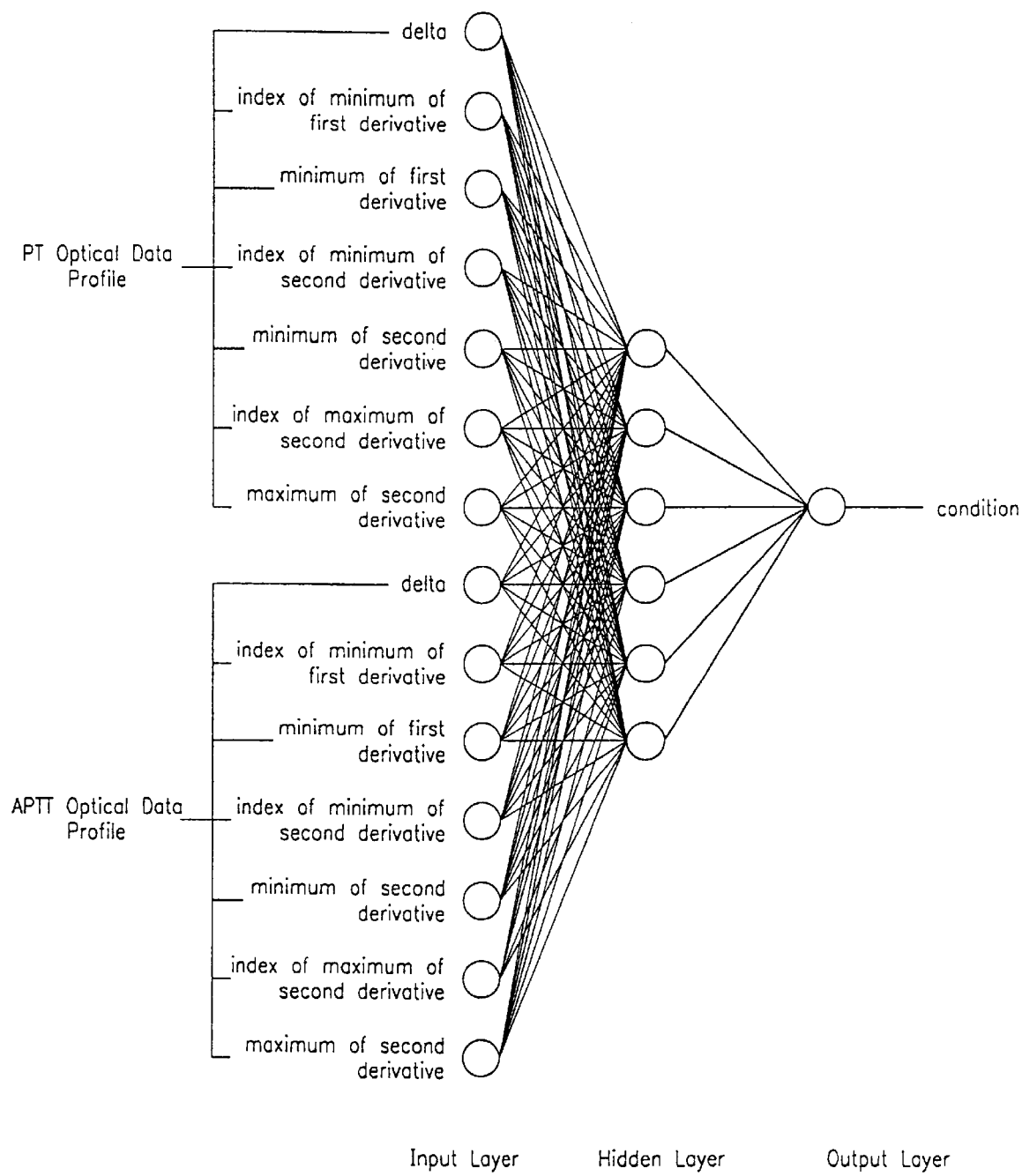
FIG. 2 is a diagram of a multilayer perceptron for predicting congenital or acquired imbalances or therapeutic conditions, relating to the neural network embodiment of the present invention.

The network configuration chosen, a multilayer perceptron (MLP) maps input predictor variables from the PT and APTT screening assays to one output variable (see FIG. 2) which represents a single specified condition. A similar network was also employed for PT-only variables and APTT-only variables. This specific MLP consists of three layers: the input layer, one hidden layer, and the output layer.

Figure 3:
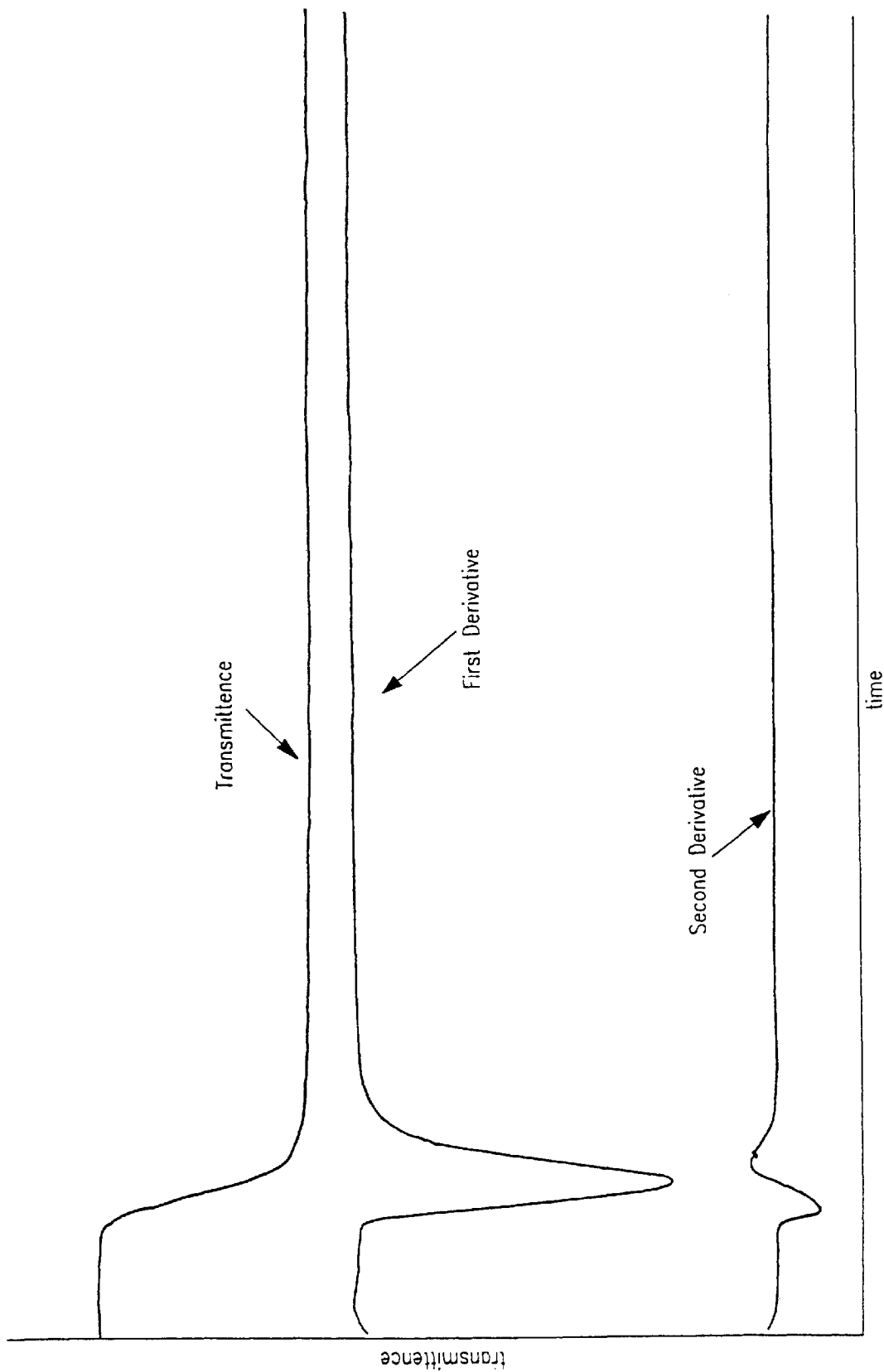
FIG. 3 is an optical profile with first and second derivatives of a normal clotting sample.

A normal optical profile is shown in FIG. 3. The set of predictor variables were chosen with the intent of describing optical profiles as completely as possible with a minimum number of variables. They are summarized in FIG. 13 where t is time from initiation of reaction, T is normalized light transmission through the reaction mixture, the $pv_{jk}$ is the kth predictor variable of assay j.

The predictor variables were scaled to values between 0 and 1, based on the range of values observed for each variable for assay type k $$i_j = f(pv_{jk},(pv_{j\ldots n,k})_{min},(pv_{j\ldots n,k})_{max}).$$

The input variable set includes $i_{1\ldots 7}$ for both a PT assay and APTT assay for each specimen. For known output variable values, heparin samples with results of greater than 0.05 units/ml were considered positive and assigned a value of 1 while negative samples were assigned a value of 0.

As the ratio of training set sample to the number of weights in a network decreases, the probability of generalizing decreases, reducing the confidence that the network will lead to correct classification of future samples taken from the same distribution as the training set. Thus, small samples sizes, then can lead to artificially high classification rates. This phenomenon is known as overtraining. In order to achieve a true accuracy rate of 80%, a guideline for the number of samples in the training set is approximately five times the number of weights in the network. For most of this work, a 14-6-1 network was used, leading to an upward bound on the sample size of O(450). To monitor and evaluate the performance of the network and its ability to generalize, a cross-validation set is processed at the end of each training epoch. This cross-validation set is a randomly determined subset of the known test set that is excluded from the training set.

Once the input predictor variables and output values were determined for all specimen optical profiles, the 757 sets of data were randomly distributed into two groups: 387 were used in the training set and 370 were used in the cross-validation set. These same two randomly determined sets were used throughout all the experiments.

All synaptic weights and threshold values were initialized at the beginning of each training session to small random numbers.

The error-correction learning rule is an iterative process used to update the synaptic weights by a method of gradient descent in which the network minimizes the error as pattern associations (known input-output pairs) in the training set are presented to the network. Each cycle through the training set is known as an epoch. The order or presentation of the pattern associations was the same for all epochs. The learning algorithm consists of six steps which make up the forward pass and the backward pass. In the forward pass, the hidden layer neuron activations are first determined $$h = F(iW1 + \theta_h)$$

where h is the vector of hidden-layer neurons, i the vector of input-layer neurons, W1 the weight matrix between the input and hidden layers, and F( ) the activation function. A logistic function is used as the activation function $$F(x) = \frac{1}{1 + e^{-x}}.$$

Then the output-layer neurons are computed $$o = F(hW2 + \theta_o)$$

where o represents the output layer, h the hidden layer and W2 the matrix of synapses connecting the hidden layer and output layers. The backward pass begins with the computation of the output-layer error $$e_o = (o-d)$$

where d is the desired output. If each element of $e_o$ is less than some predefined training error tolerance vector $TE_{tol}$, than the weights are not updated during that pass and the process continues with the next pattern association. A training error tolerance of 0.1 was used in all experiments unless otherwise specified. Otherwise, the local gradient at the output layer is then computed:

$$g_o = o(1-o)e_o.$$

Next, the hidden-layer local gradient is computed:

$$g_h = h(1-h)W2g_o.$$

Once the hidden layer error is calculated, the second layer of weights is adjusted $$W2_m = W2_{m-1} + \Delta W2$$

where $$\Delta W2 = \eta h g_o + \gamma \Delta W2_{m-1}$$

is the learning rate, $\gamma$ is the momentum factor, and m is the learning iteration. The first layer of weights is adjusted in a similar manner $$W1_m = W1_{m-1} + \Delta W1$$

where $$\Delta W1 = \eta i e + \gamma \Delta W1_{m-1}.$$

The forward pass and backward pass are repeated for all of the pattern associations in the training set, referred to as an epoch, 1000 times. At the end of each epoch, the trained network is applied to the cross-validation set.

Several methods were employed to measure the performance of the network's training. Error, E, for each input set was defined as $$E = \sqrt{\frac{1}{N}\sum_{q=1}^{N}(d_q - o_q)^2}.$$

The learning curve is defined as the plot of E versus epoch. The percent classification, $\phi$, describes the percent of the total test set (training and cross-validation) that is correctly classified based on some defined decision boundary, $\beta$. Receiver-Operating Characteristic (ROC) plots have also been utilized to describe trained networks' ability to discriminate between the alternative possible outcome states. In these plots, measures of sensitivity and specificity are shown for a complete range of decision boundaries. The sensitivity, or true-positive fraction is defined as $$\text{sensitivity} = \frac{\text{true positive}}{\text{true positive} + \text{false negative}}$$

and the false-positive fraction or (1-specificity) is defined as $$(1 - \text{specificity}) = \frac{\text{false positive}}{\text{false positive} + \text{true negative}}.$$

These ROC plots represent a common tool for evaluating clinical laboratory test performance.

Using the test set described, experiments were performed to determine if the presence of heparin could be predicted with this method. First, experiments were conducted to determine optimal error-correction backpropagation learning parameters: (1) hidden layer size, (2) learning rate, and (3) momentum. Additional experiments were also conducted to compare the performance of networks based on PT and APTT assays alone with that of one combining the results of both, the effect of the training error tolerance, and the decision boundary selection.

FIG. 9 shows the effect of the hidden layer size on the training and cross validation error and the percent correct classification for the optimal decision boundary, defined as the decision boundary which yielded the lowest total number of false positives and false negatives from the total test set. As the hidden layer size is increased, the error is decreased. However, the ability to generalize does not increase after a hidden layer size of 6. The most significant benefit in terms of both error and percentage correct classification is between 4 and 6. A hidden layer size of 6 was used for the remainder of the experiments.

Figure 4:
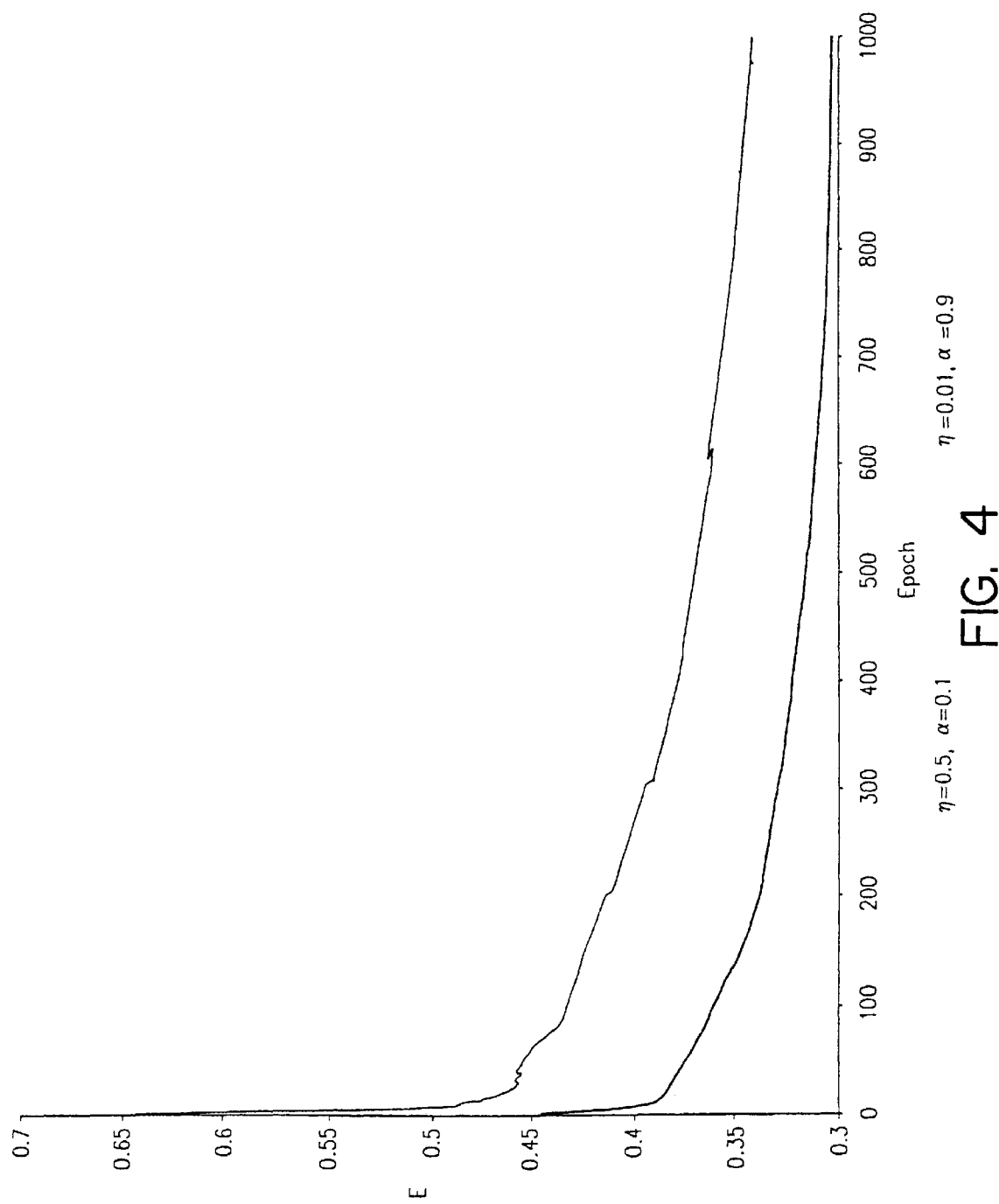
FIG. 4 is an illustration of two learning curves.

A series of experiments were conducted with $\eta=\{0.01, 0.1, 0.5, 0.9\}$ and $\gamma=\{0.0, 0.1, 0.5, 0.9\}$. FIG. 4 shows the learning curves for two of the best combinations of parameters.

Figure 5:
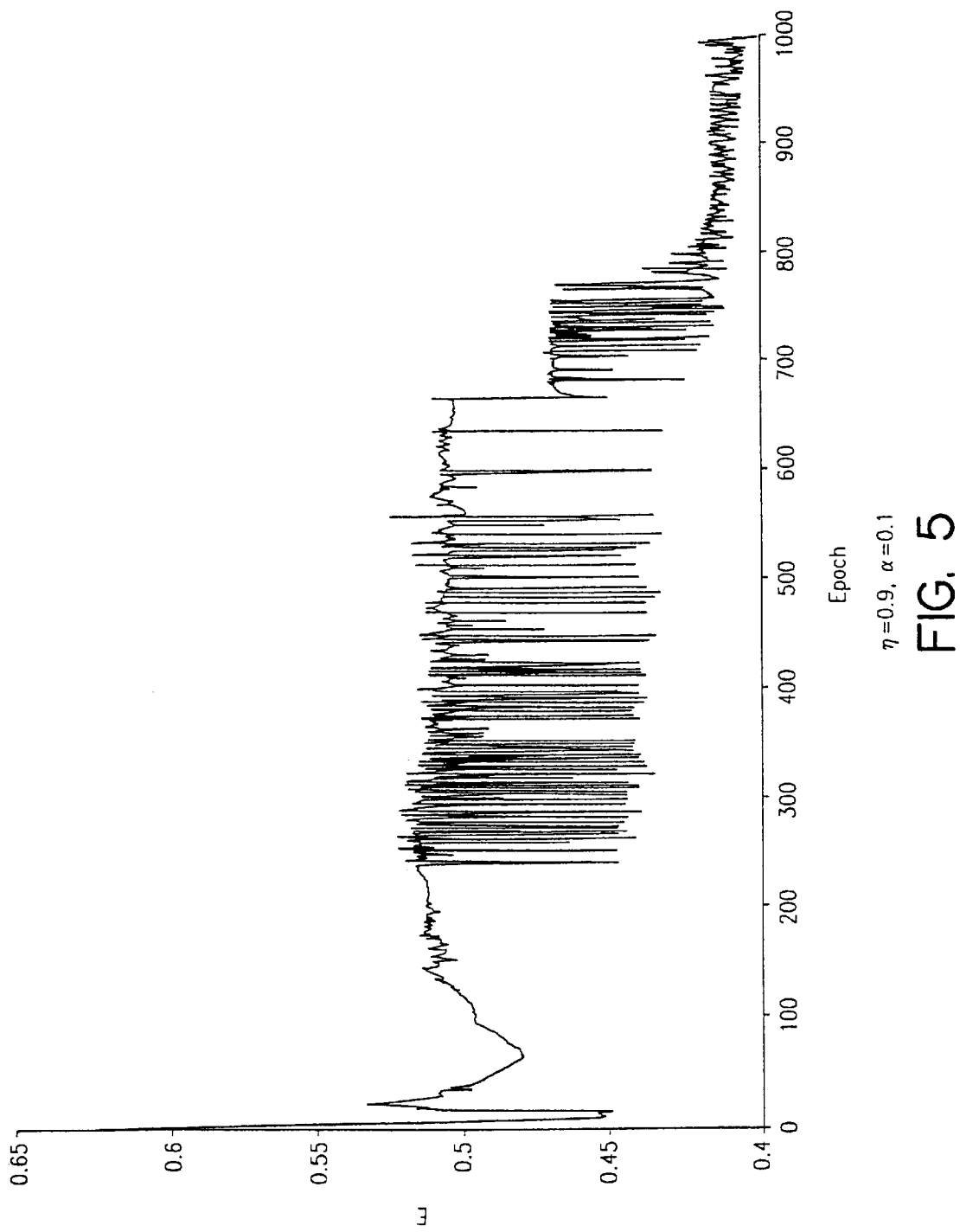
FIG. 5 is an illustration of an unstable learning curve.

FIG. 5 shows an example learning curve when the learning rate is so high it leads to oscillations and convergence to a higher E. In general, as $\eta \rightarrow 0$ the network converged to a lower E and as $\gamma \rightarrow 1$, the rate of convergence improved. As $\eta \rightarrow 1$, the value of E converged too increased and oscillations increased. In addition, as $\eta \rightarrow 1$, $\gamma \rightarrow 1$ exacerbated the oscillations.

Figure 6:
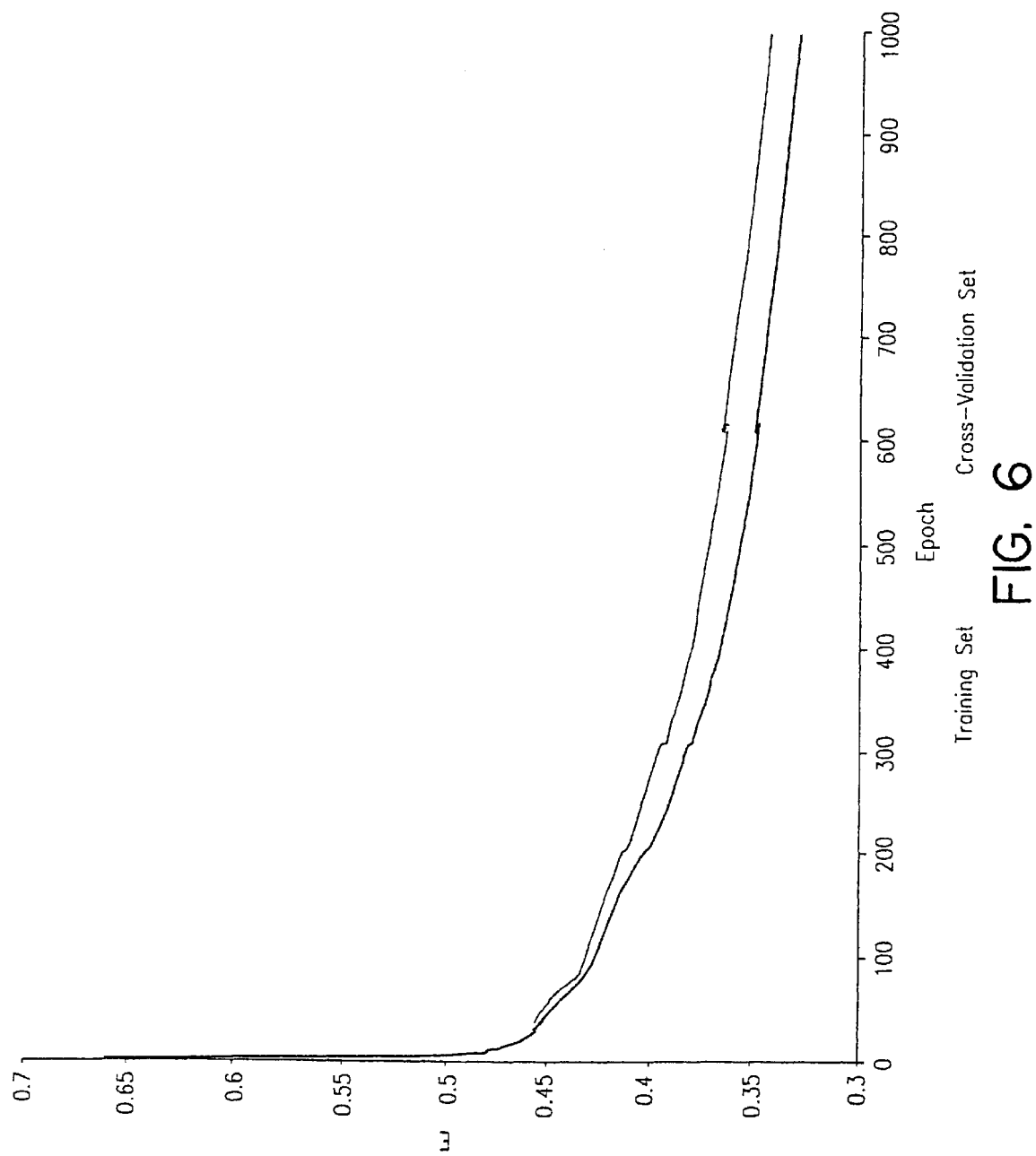
FIG. 6 is a graph showing a comparison of training and cross-validation learning curves.

FIG. 6 shows a comparison of the learning curve for the training set and cross-validation set for $\eta=0.5$ and $\gamma=0.1$. It is a primary concern when developing neural networks, and it has been previously shown that it is important to look not only at the error in the training set for each cycle, but also the cross-validation error.

Figure 7:
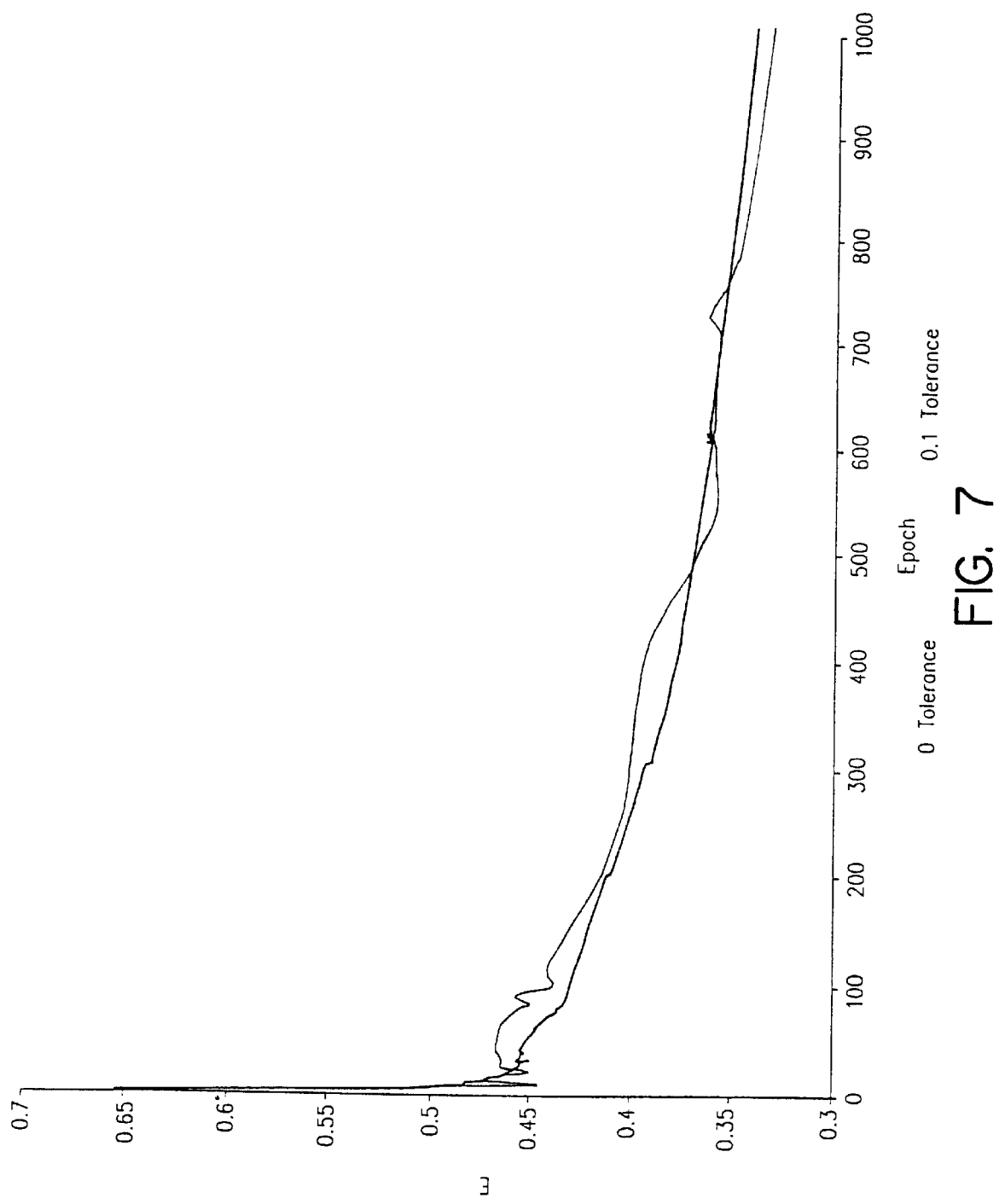
FIG. 7 is a graph showing a comparison of training error for training tolerances of 0.0 and 0.1.

FIG. 7 shows the learning curve $\eta=0.5$ and $\gamma=0.1$ and a learning tolerance of 0.0 and 0.1. These results suggest that a small learning tends to smoothen the convergence of the learning process.

Figure 8:
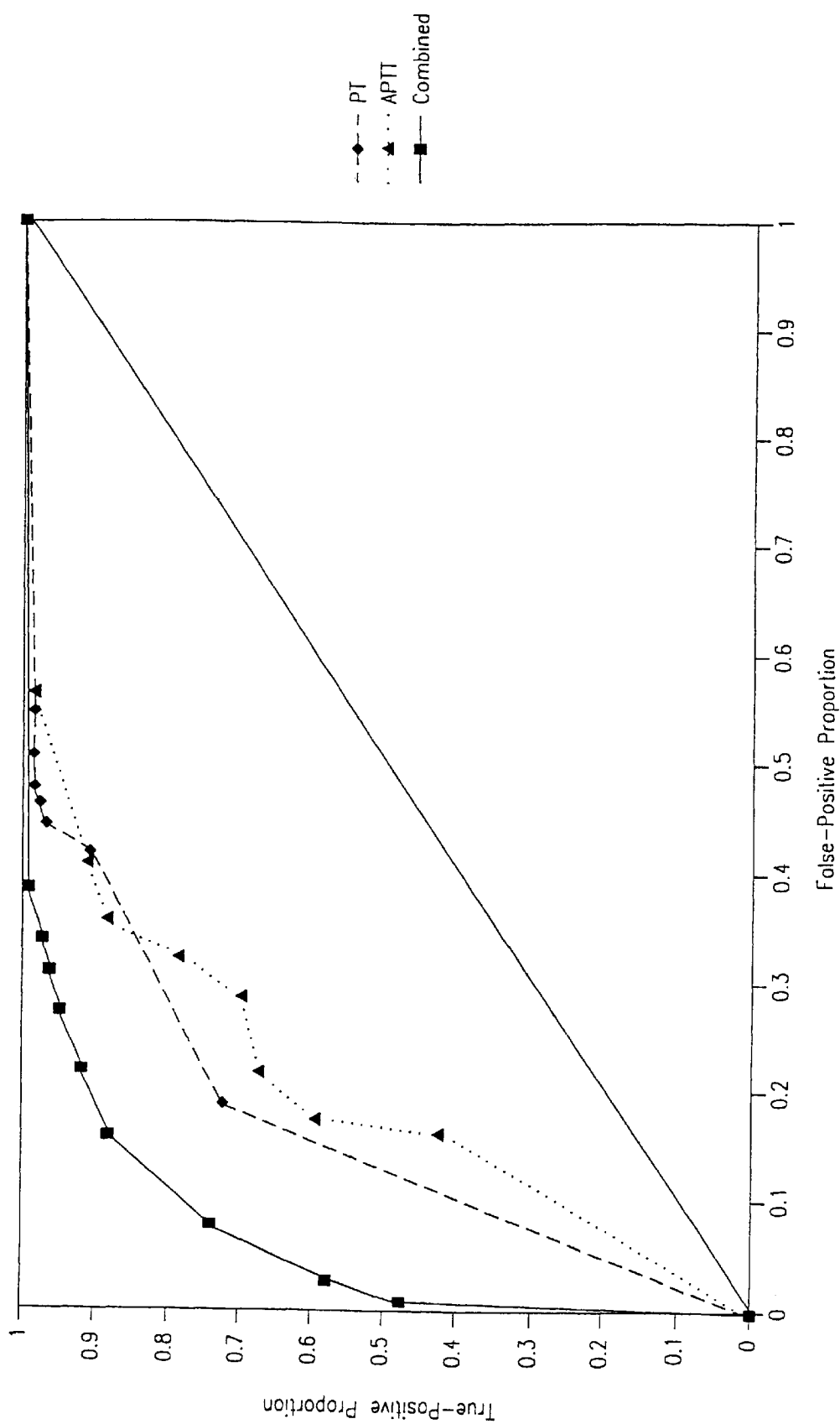
FIG. 8 is a receiver operator characteristic (ROC) illustrating the effect of decision boundary on classification.

FIG. 8 shows the ROC plot for networks trained with the predictor variables from each of the two screening assays with that of them combined. In the single assay cases, the hidden layer size was 3. While using the data from one assay does lead to some success, using the information from both assays makes a significant improvement in the ability of the network to correctly predict the presence of heparin. This graph indicates that a 90% true positive proportion can be achieved with a false positive proportion of 15%. Using a single assay, a 60–70% true positive proportion can be achieved with a false positive proportion of approximately 15%.

EXAMPLE 2

Factor VIII

Figure 10:
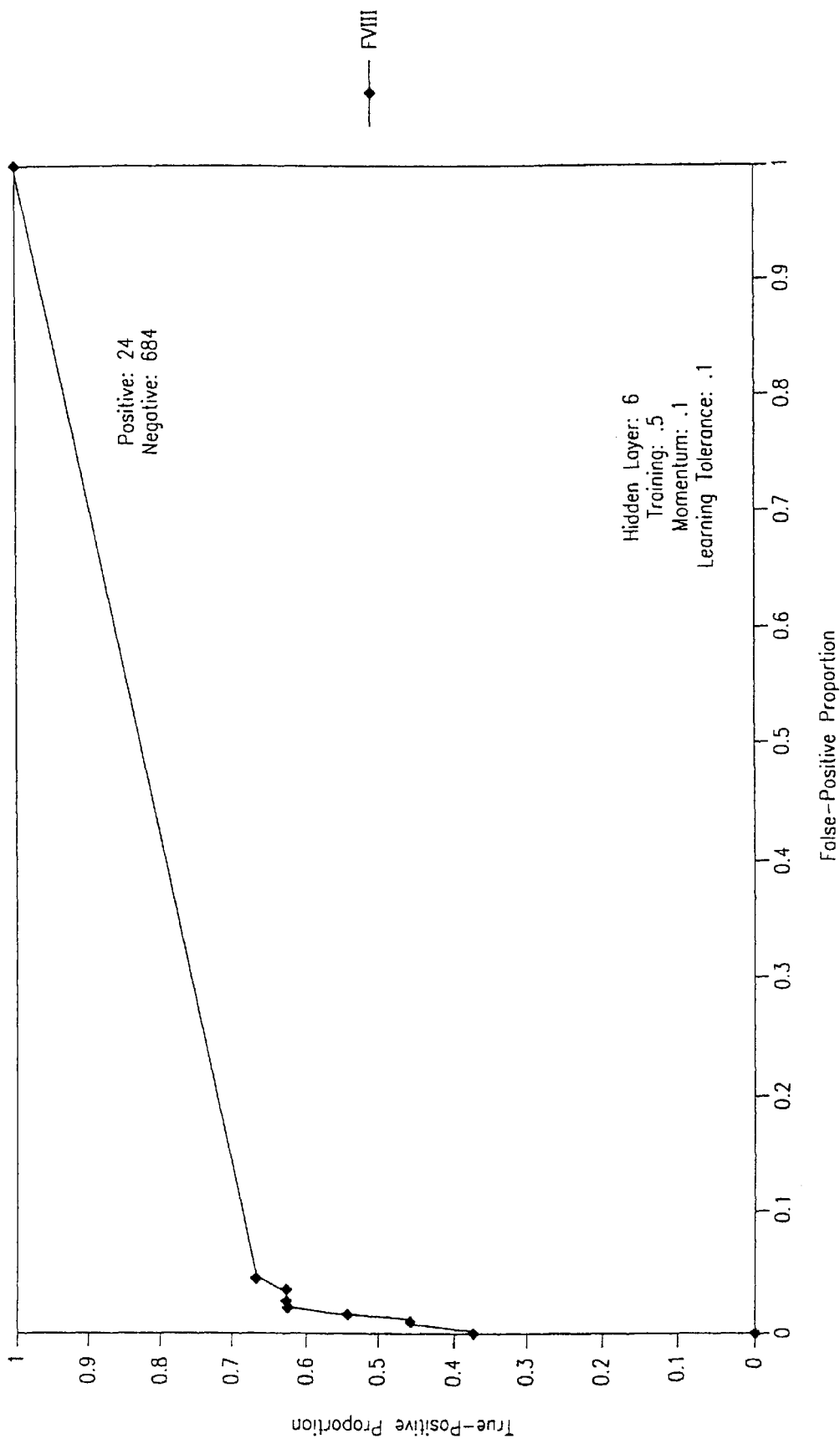
FIG. 10 is a receiver operator characteristic plot related to predicting an abnormality in relation to Factor VIII.
Figure 11:
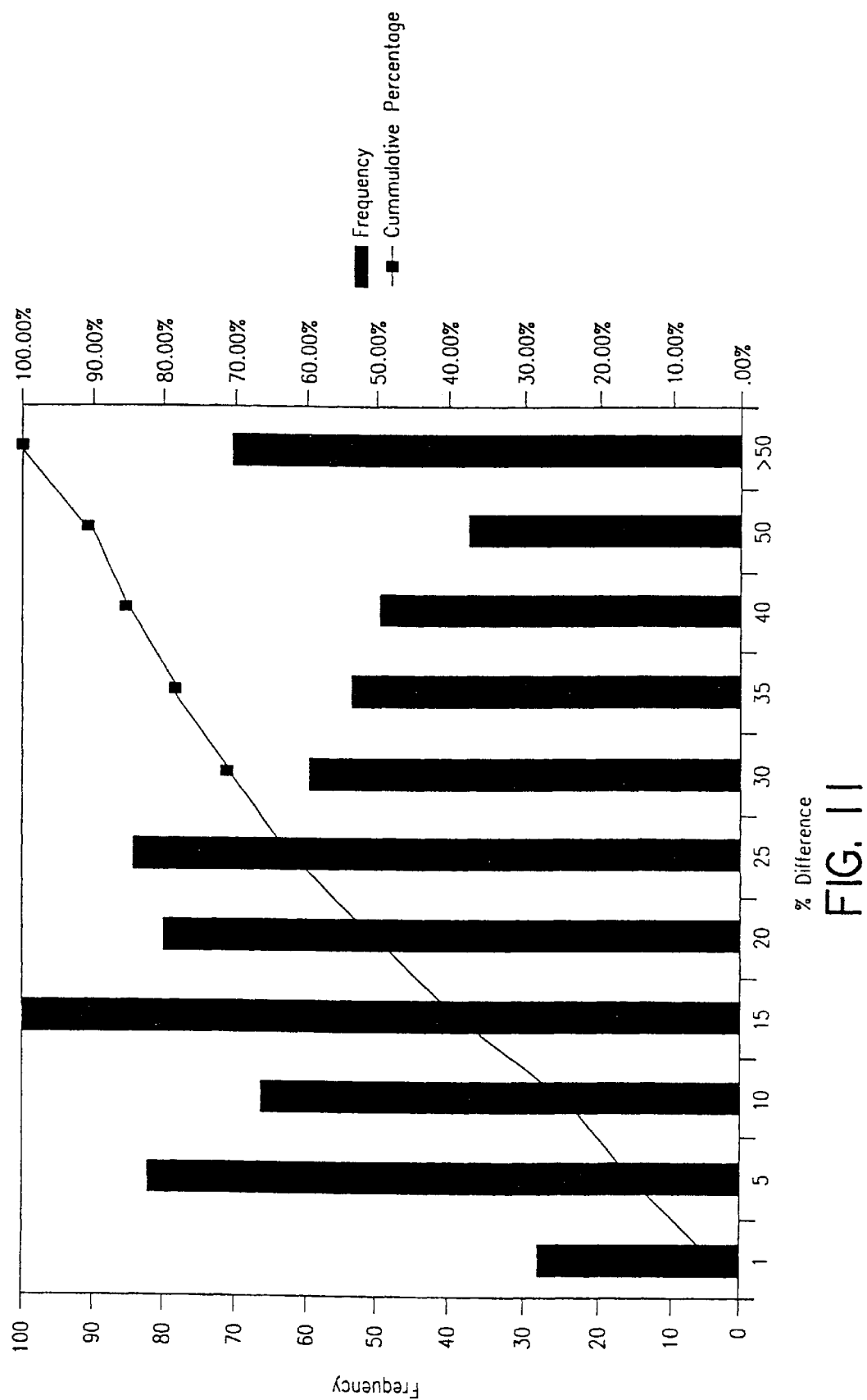
FIG. 11 is a graph demonstrating the ability to predict actual Factor VIII activity.

Similar tests were run as in Example 1. As can be seen in FIGS. 10 and 11, two training sessions were conducted for predicting a Factor VIII condition in an unknown sample. FIG. 10 is a receiver operator characteristic plot related to predicting an abnormality in relation to Factor VIII. In FIG. 10, everything below 30% activity was indicated as positive, and everything above 30% was indicated as negative. Cutoff values other than 30% could also be used. In this Example, the activity percentage has a known accuracy of approximately + or −10%. In FIG. 11, the actual percent activity was utilized as the output.

EXAMPLE 3

Factor X

Figure 12:
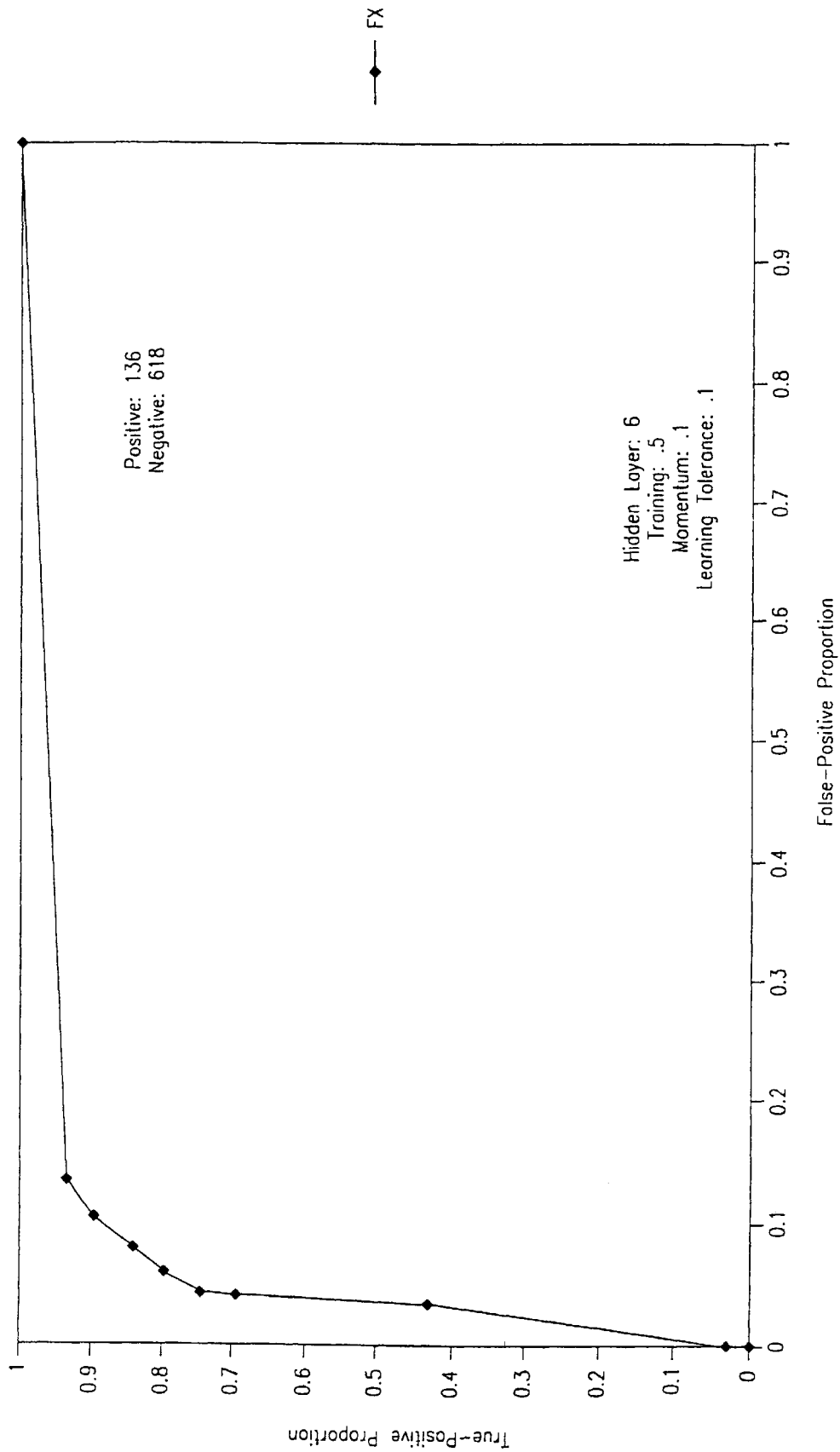
FIG. 12 is a receiver operator characteristic plot related to predicting an abnormality in relation to Factor X.

As can be seen in FIG. 12, the method of the present invention was run similar to that as in Example 2, where here an abnormality in Factor X concentration was predicted from unknown samples. Everything below 30% activity was indicated as positive, and everything above 30% was indicated as negative. Cutoff values other than 30% could also be used.

The results of the cross-validation sample sets throughout the experiments indicate that the sample size was sufficient for the network to generalize. While the random distribution of the training and cross-validation sets were held constant throughout the experiments presented, other distributions have been used. These distributions, while all yielding different results, still lead to the same general conclusion.

Many alternatives for or additions to the set of predictor variables were explored. This included coefficients of a curve fitted to the data profile, pattern recognition, and clot time-based parameters. Low order functions tend to lose information due to their poor fit, and high order functions tend to lose information in their multiple close solutions. Clot-based parameters, such as clot time, slope in the section prior to the initiation of clot formation, and afterwards, are often available, but not always (because in some samples, the clot time is not detectable). The successful results observed indicate that the set of predictor variables used are effective for predicting congenital or acquired imbalances or therapeutic conditions.

The optimization of the network learning algorithm's parameters made significant differences in its performance. In general, performance was best with low learning rates, high momentum rates, some small training error tolerance, and a hidden layer size approximately half of the size of the input layer.

ADDITIONAL EXAMPLES optical measurements for APTT and PT assays were performed on MDA 180 instruments at a wavelength of 580 nm. Plasma specimens (n=200) included normal patients, patients with a variety of coagulation factor deficiencies and patients undergoing heparin or other anticoagulant therapy. Duplicate APTT and PT screening assays were performed on each specimen with two MDA 180s using single lots of APTT and PT reagents. These specimens were also analyzed using specific assays for FII, FV, FVII, FVIII, FIX, FX, FXI, FXII, heparin, fibrinogen, plasminogen, protein C and antithrombin-III.

Data Processing and Neural Networks

Optical profile data files were exported from the MDA 180s and processed off-line. A set of nine parameters was derived to describe the timing, rate and magnitude of coagulation events. These parameters were calculated for all APTT and PT tests. The parameter set is modified slightly from that for Example 1. In this approach, the optical data for a PT or APTT assay was divided into three segments (a pre-coagulation segment, a coagulation segment and a post-coagulation segment) using divisions based on the minimum and maximum value of the second derivative for changes in optical signal with respect to time. The parameters that were analyzed included: (1) the times at which the onset, midpoint and end of the coagulation phase occur (tmin2, tmin1 and tmax2; respectively); (2) mean slopes for the pre-coagulation phase and the post-coagulation phase (slope1 and slope3, respectively) and the slope at the mid-point of coagulation (min1, the coagulation "velocity" at reaction midpoint, which is analogous to slope2); (3) terms for coagulation "acceleration" and "deceleration" (min2 and max2, respectively); and (4) the magnitude of signal change during coagulation (delta).

Three different sets of data parameters were used as input to the neural network: (1) the nine parameters from PT assays, (2) the nine parameters from APTT assays, and (3) the combined parameters from the APTT and PT assays. Each specimen was run in duplicate on two instruments, to give a total of approximately 800 parameter sets from the 200 specimens. The total number varied slightly because of missing data due to insufficient sample, mechanical failure or unspecified failures. The data parameter sets were divided into training and cross-validation sets randomly by specimen where all replicates for a given specimen were grouped either in the cross-validation set or training set. The same training and cross-validation sets were used throughout this study. The method for training and cross-validation of the back-propagation neural networks has been described in relation to Example 1. Each neural network was trained for 1000 epochs. Training parameters were learning rate, 0.01; momentum, 0.5; learning tolerance, 0.10; decay, 0.05; input layer size, 18 (or 9 for single assays); hidden layer size, 9 (or 5 for single assays); and output layer size, 1. Three types of networks were trained. These included networks that classified specimens as deficient or non-deficient based on a single diagnostic cut-off, sets of networks that used diagnostic cut-offs at different levels of the same factor, and networks trained to estimate the actual concentration of a specific factor.

Figures 21, 22:
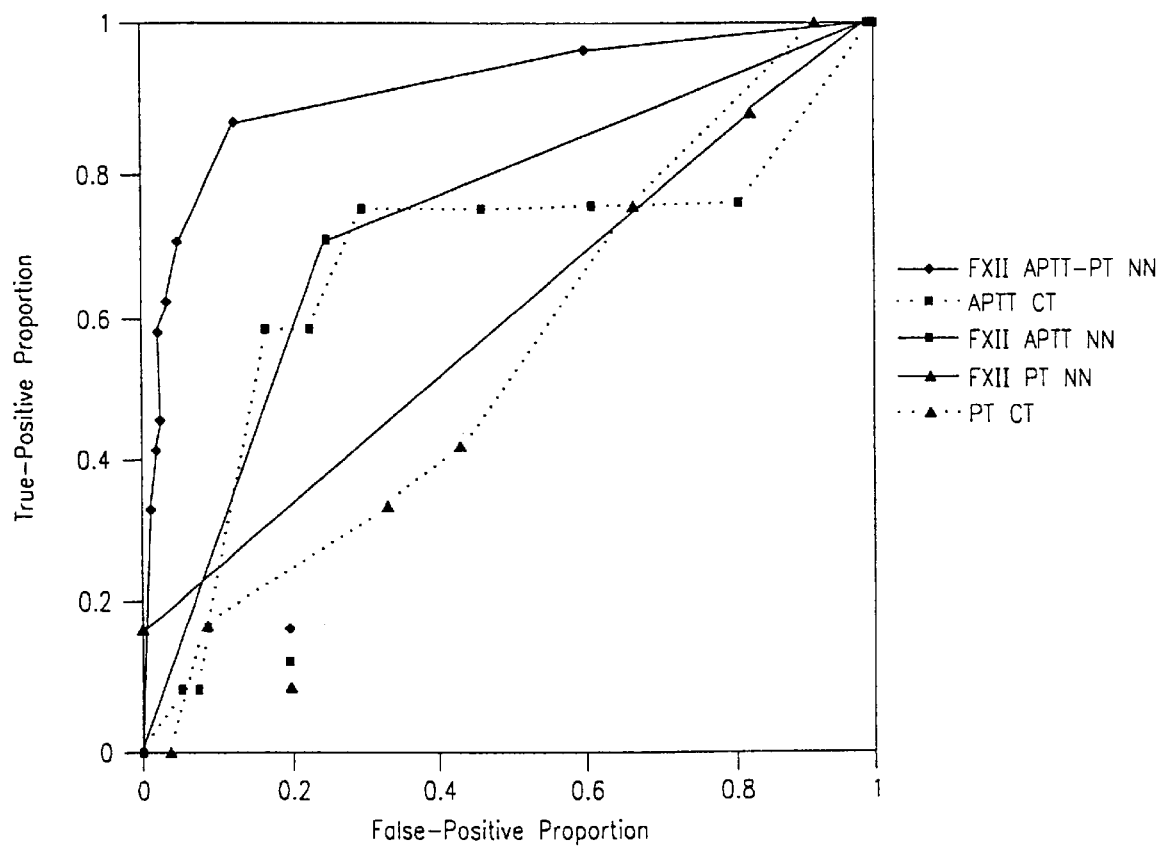
FIG. 22 shows the constituency of the training and cross-validation sets with regard to each factor deficiency.

Classification of Factor Deficiencies Based on a Single Diagnostic Cut-Off Level In the first set of tests, neural networks were trained to classify plasma samples into two groups, positive (factor-deficient) and negative (non-deficient), and results were compared to classification based on the measured factor concentration for the specimens. In most testing, the diagnostic cut-off for defining factor deficiencies was set as 30%; that is, specimens with a measured concentration of less that 30% of normal for a specific factor were defined as deficient and those with greater than 30% activity were defined as non-deficient. These diagnostic cut-off levels were arbitrarily defined, but are based on clinical requirements and reagent sensitivity. The desired output from positive samples and negative samples were defined as '1' and '0', respectively; the actual output for each specimen was a floating point value, a, where $0 \leq a \leq 1$. FIG. 22 shows the constituency of the training and cross-validation sets with regard to each factor deficiency. Classification of specimens was evaluated at varying "decision boundaries" that divided the neural network outputs into positive and negative groups. This positive or negative classification was then compared to the desired output (the known classification) for each input data set. Results were plotted as nonparametric receiver-operating characteristic (ROC) curves and the areas under the curves were computed along with their associated standard errors. ROC curves were also derived for APTT and PT clot time values for comparison. Data points on the ROC curves represent the proportion of true-positive and false-positive classifications at various decision boundaries. Optimum results are obtained as the true-positive proportion approaches 1.0 and the false-positive proportion approaches 0.0 (upper-left corner of graph). The optimum global measure of the ROC curve is an area of 1.0.

Classification of Factor Deficiencies at Multiple Diagnostic Cut-Off Levels

A second set of networks was trained for FX classification in a similar manner to the first set except that the diagnostic cut-off level was varied (10%, 30%, and 50%). FX was chosen for this experiment because the data set contained a greater number of positive samples at all cut-off levels than other factors.

Estimation of Factor Concentration Using Neural Networks

A third set of networks were trained to approximate actual specific factor activities (FII, FV, FVII, FVIII, FIX, FX, FXI and FXII) and fibrinogen levels from combined PT and APTT parameters from unknown samples. In these cases, the desired output of the training and cross-validation sets was the measured activity for a specific factor for each specimen and the actual output of the neural network was a predicted concentration for this specific factor activity. The coefficients of linear regressions using the desired outputs versus the actual neural network outputs for the cross-validation set were used to describe the performance of these networks. The Pearson product moment correlation coefficient, r, was used to estimate the correlation between the two data sets.

Classification of Factor Deficiencies Based on a Single Diagnostic Cut-Off Level Neural networks were trained to classify samples as deficient (positive result) or non-deficient (negative result) for individual plasma factors, using a value of 30% activity as the diagnostic cut-off to define deficiencies. Results were examined graphically using receiver-operating curves (ROC). These graphs plot the true-positive proportion (number of positives detected divided by the total number of positives) versus the false-positive proportion (number of negative specimens incorrectly diagnosed as positive divided by the total number of negatives). An ROC curve is generated by determining true-positive and false-positive proportions at different "decision boundaries" for the diagnostic test. For example, an ROC plot for diagnosis of FII deficiencies using PT clot time was generated by varying the decision boundary (value of PT clot time) used to differentiate between deficient and non-deficient specimens. When a short clot time is used as the decision boundary, most deficient specimens can be identified but a significant proportion of non-deficient specimens may also be flagged (false-positives). When a long clot time is used as the decision boundary, the proportion of false-positives decreases, but the number of true-positive specimens that are not diagnosed may also increase. Under ideal conditions, a decision boundary can be identified from an ROC curve that produces a very high proportion of true-positives and a very low proportion of false-positives. This condition corresponds to the upper left region of the ROC plot. Two related terms that are often applied to clinical diagnostic tests are "sensitivity" and "specificity". Sensitivity refers to the ability to detect positive specimens and corresponds to the y-axis of the ROC plots. Specificity refers to the proportion of specimens diagnosed as negative which are correctly identified. The ROC x-axis equals (1-specificity). Visual assessment of the ROC curves is one method used to evaluate the performance of the neural networks and compare them to the diagnostic power of PT and APTT clot times. Another method is to measure the diagnostic performance by using the area under the ROC curves. The area under the ROC curve is equivalent to an estimate of the probability that a randomly chosen positive specimen will have a more positive result than a randomly chosen negative specimen. In the event that ROC curves overlap, the shape of the curves as well as the areas beneath them becomes important. An ROC curve encompassing a smaller area may be preferable to an overlapping curve with greater area depending on the desired performance for a given diagnostic system.

FIGS. 14–21 show ROC curves for neural networks trained to predict FII, FV, FVII, FVIII, FIX, FX, FXI, and FXII deficiencies from PT parameters alone, from APTT parameters alone, or from combined APTT and PT parameters. ROC plots based on classification using APTT and PT clot times are included for comparison. FIG. 23 shows the area under these curves and their associated standard errors.

Figure 14:
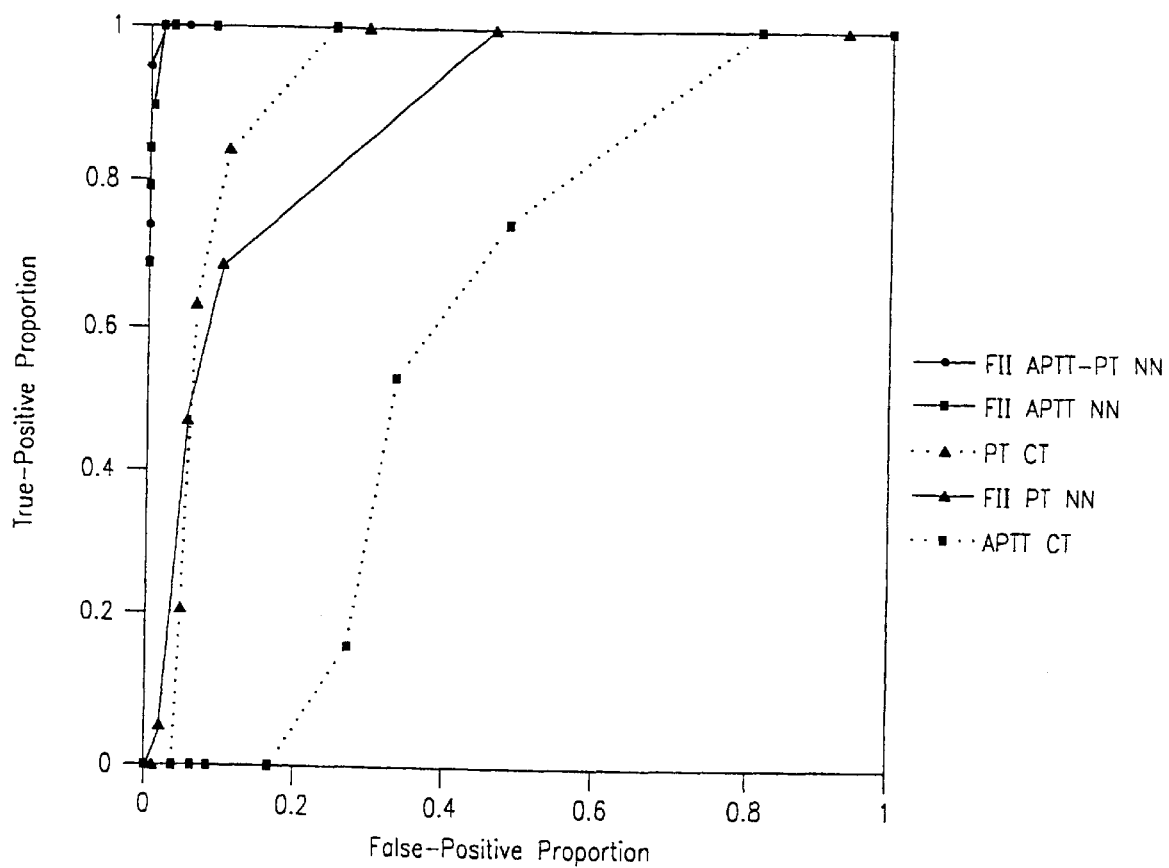
FIGS. 14–21 show ROC curves for neural networks trained to predict FII, FV, FVII, FVIII, FIX, FX, FXI, and FXII deficiencies from PT parameters alone, from APTT parameters alone, or from combined APTT and PT parameters.

Results for classification of FII deficiencies are shown in FIG. 14. Best results were observed for neural networks using APTT parameters alone or combined with PT parameters, with area under ROC curves greater than 0.99 in both cases (FIG. 23). Classification based on PT or APTT clot times, or from neural networks using PT data alone resulted in less successful classification and reduced area under curves.

Figure 15:
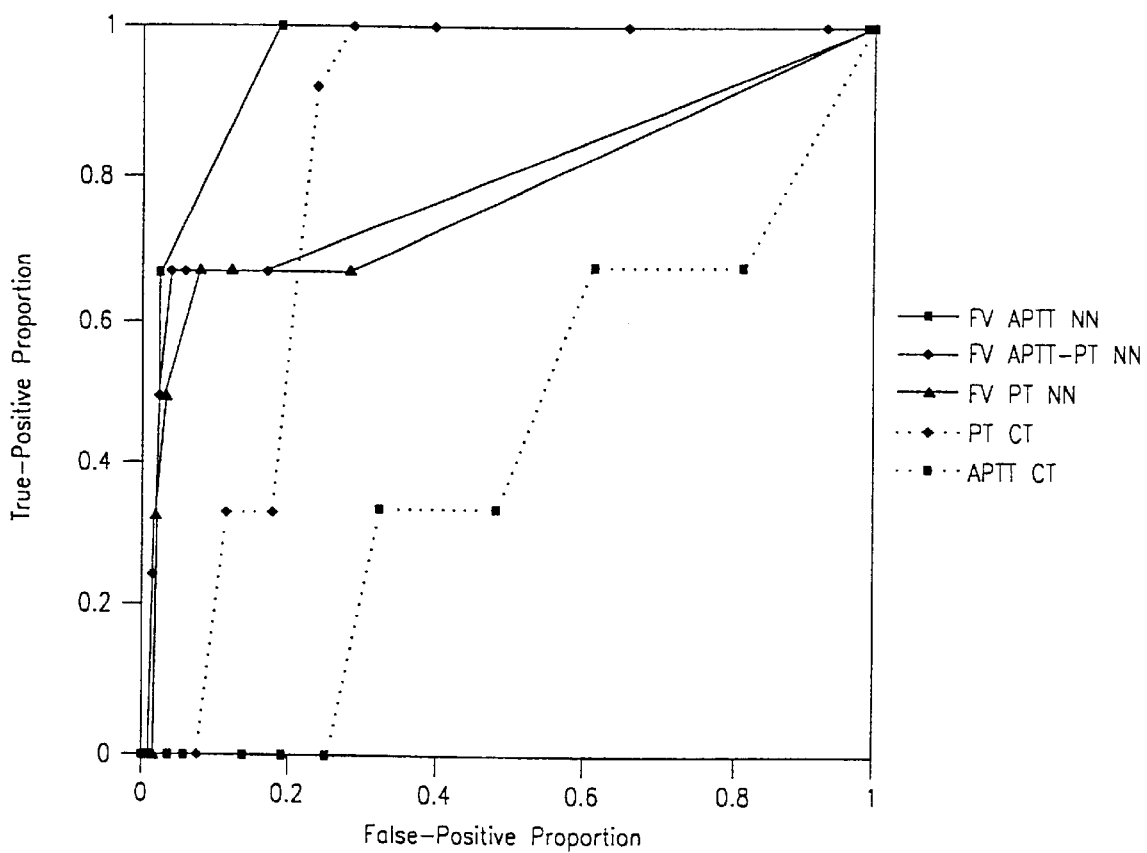
Figure 16:
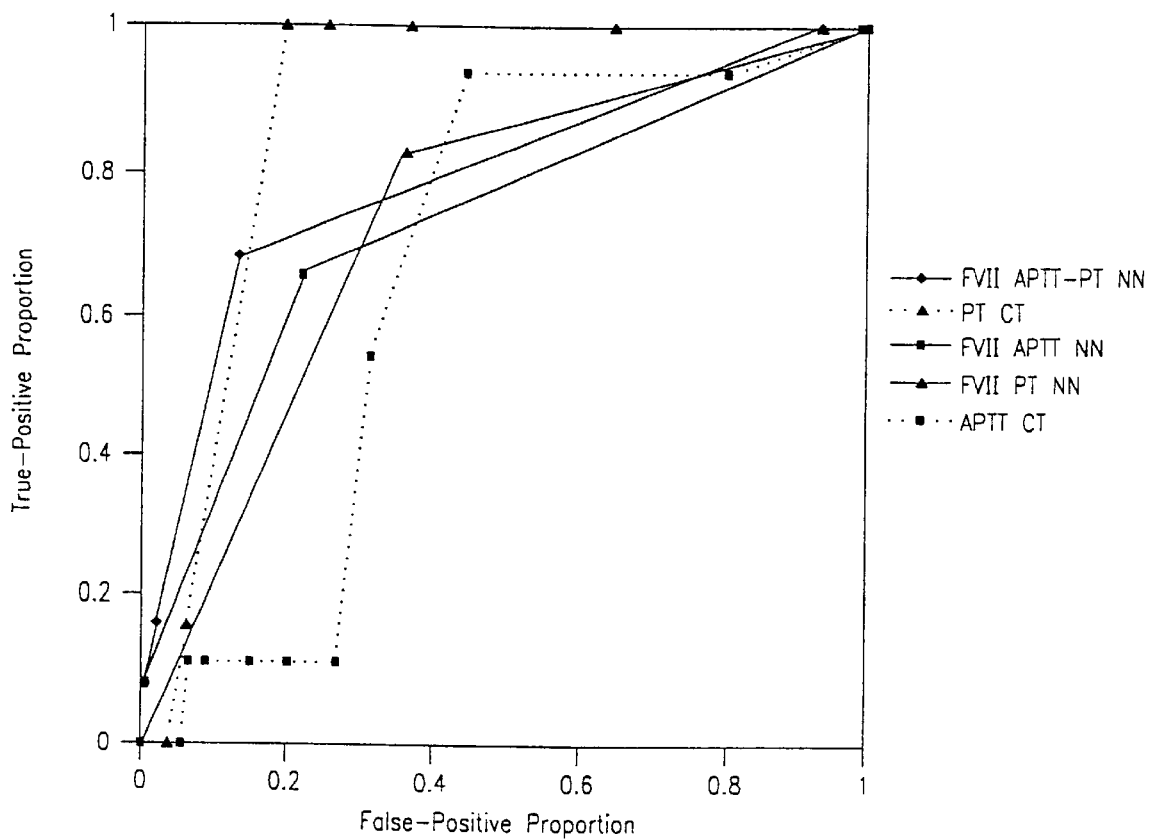
Figure 17:
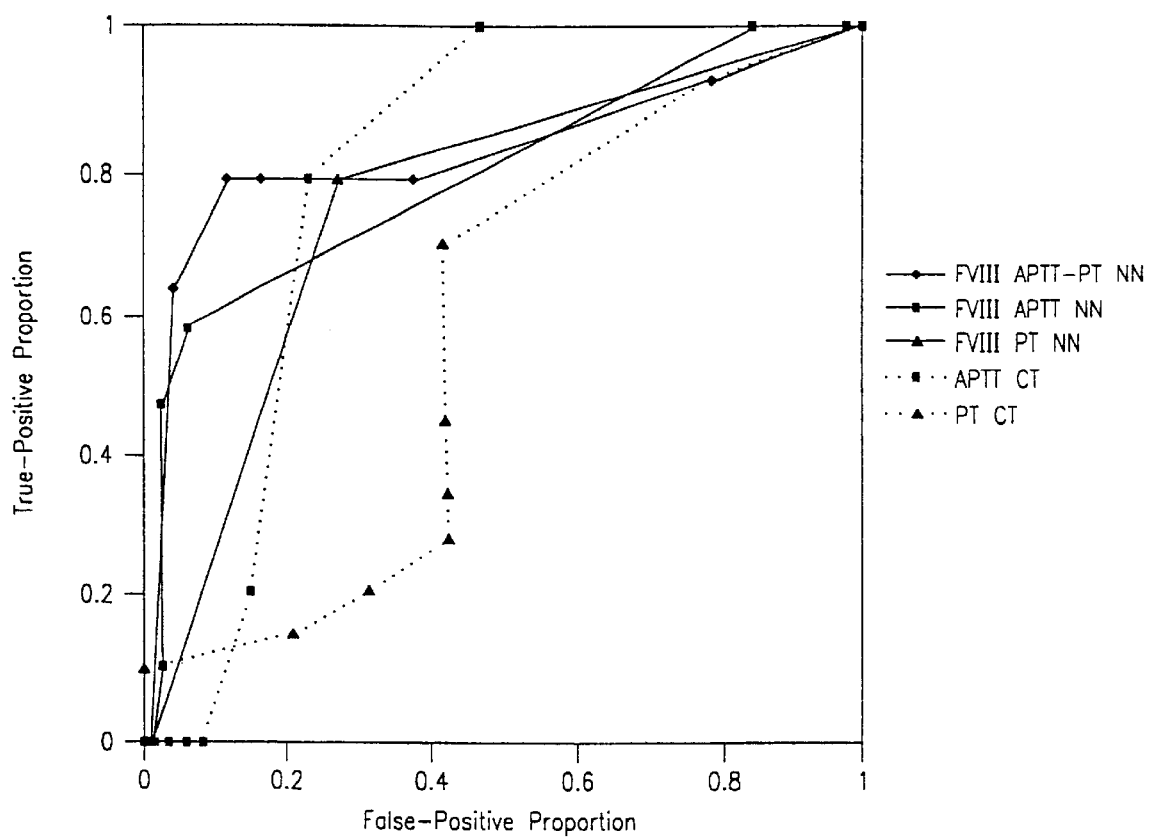
Figure 18:
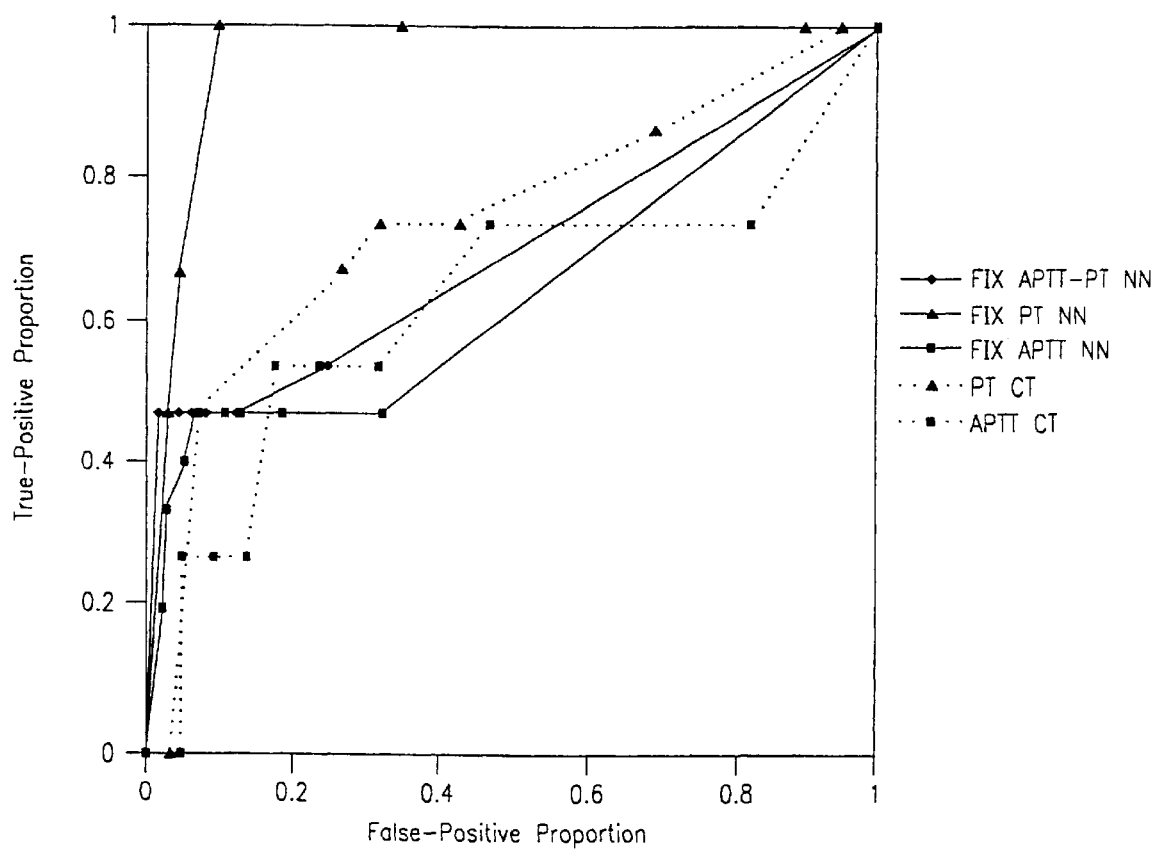
Figure 19:
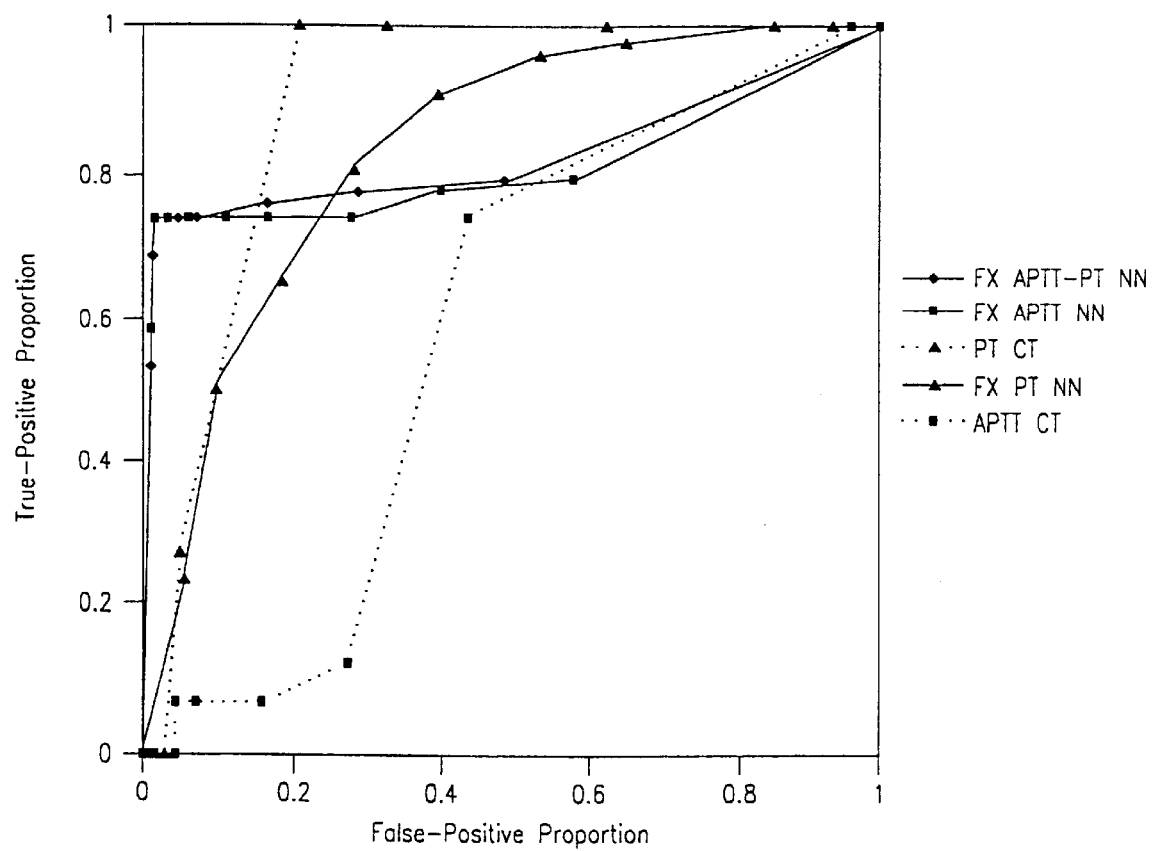
Figure 20:
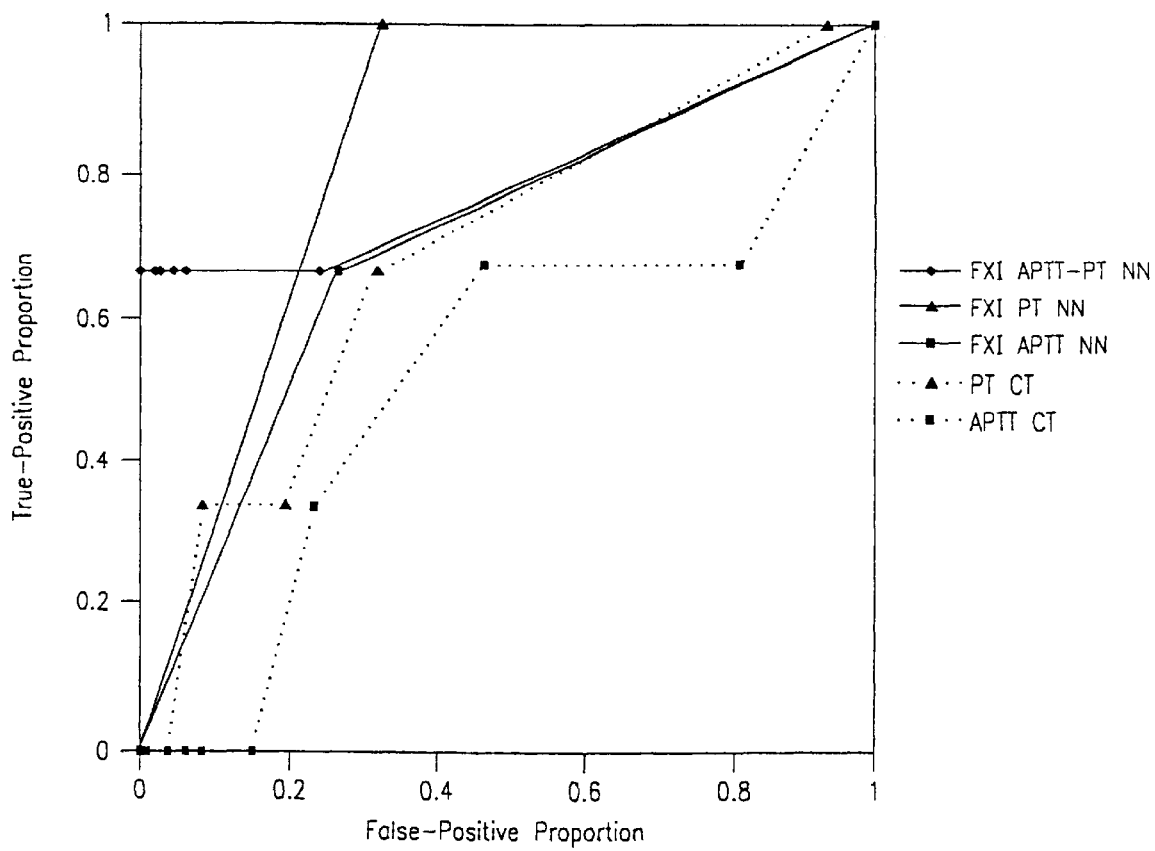

Results from classification of FV deficiencies showed somewhat different characteristics (FIGS. 15 and 23). Best results were observed for classification from a neural network using APTT data parameters, based on visual inspection and area under the ROC curve. Less successful classification were obtained from neural networks using PT data parameters alone or combined with APTT data, and from PT clot time, as judged from areas under ROC curves. Classification based on PT clot time was qualitatively different from neural networks using PT data, however, and tended toward higher sensitivity rather than specificity. This type of pattern was observed for classification of several coagulation factors, especially factors VIII, X and XI. In situations where overlapping ROC curves were obtained, consideration of the relative value of specificity and sensitivity, as well as the area under ROC curves, becomes important in comparing diagnostic results.

For several of these plasma factors, including FV, FVIII, FIX, FX, FXI and FXII (FIGS. 15, 17, 18, 19, 20 and 21), it appeared that it would be possible to achieve a moderately high true-positive proportion (>0.6) while maintaining a low false-positive proportion (<0.1) from neural networks using PT, APTT or combined parameters. This corresponds to a situation where a significant proportion of deficient specimens are not detected (moderate sensitivity), but those that are detected are correctly classified as deficient for that specific factor (high specificity). In contrast, using PT or APTT clot times it was possible for most factors to adjust decision boundaries to identify most deficiencies (true-positive proportion approaching 1.0, high sensitivity), but with a relatively high rate of false-positives (low specificity). This corresponds to a situation where most or all deficient specimens are detected, but where the specific factor deficiency is frequently not correctly identified. The first scenario involving moderate or high true-positive rates with very low false positive rates may be preferable in the diagnostic scheme shown in FIG. 13.

For factors II, V, IX and XII, it appeared that an appropriate choice of neural network gave best diagnostic performance, as judged from the area under curves. For factors VIII, X and XI, neural networks were not visibly superior to diagnosis based on clot times when areas under ROC curves were the only consideration; however, neural networks for these factors did provide better specificity. For one factor (FVII, FIG. 16), neural network classification was less effective than for other factors, at least in this test system.

The performance of networks using data parameters from PT or APTT assays alone or in combination varied for different factors. For factors VIII and XII, best performance (significantly greater area with no overlap) was observed when the combined sets of APTT-PT data parameters were used. For several other factors, use of a single parameter set provided results that were comparable to or better than the combined APTT and PT parameters. A network using only APTT data parameters (APTT NN) was equivalent (similar area) to a network using combined APTT-PT data (APTT-PT NN) for FII and FX; and superior for FV (greater area and no overlap). Networks using only PT parameters provided results that were comparable (similar area) to the combined parameters for FV classification and better (greater area and insignificant overlap) for FIX classification.

The data for misclassified positive specimens were examined more closely. Misclassified positive specimens were clustered in several categories: 1) Specimens with "no clot" APTT or PT results (specimens with very prolonged or very weak coagulation reaction for which no clot time can be reliably calculated); 2) specimens with multiple deficiencies or abnormalities; 3) specimens with borderline deficiencies (factor activity marginally lower than the diagnostic cut-off of 30%); and 4) specimens with atypically steep slope during the pre-coagulation phase for APTT assays that were not characteristic of other specimens in the same classification (FX deficiencies were not detected for two specimens exhibiting this characteristic with FX activities of 26.8% and 16.8%, respectively).

Classification of Factor Deficiencies at Multiple Diagnostic Cut-Off Levels

The ability of neural networks to classify FX-deficient specimens was tested at varying diagnostic cut-offs. Areas under the ROC curves for cut-off levels of 10%, 30% and 50% FX activity are shown in FIG. 24. Results indicate that progressively poorer classification (as expressed in smaller areas under ROC curves) was observed as higher cut-off levels were used. This was true for classification based on neural networks or PT clot times.

Neural Network Estimation of Factor Concentration

Figure 26:
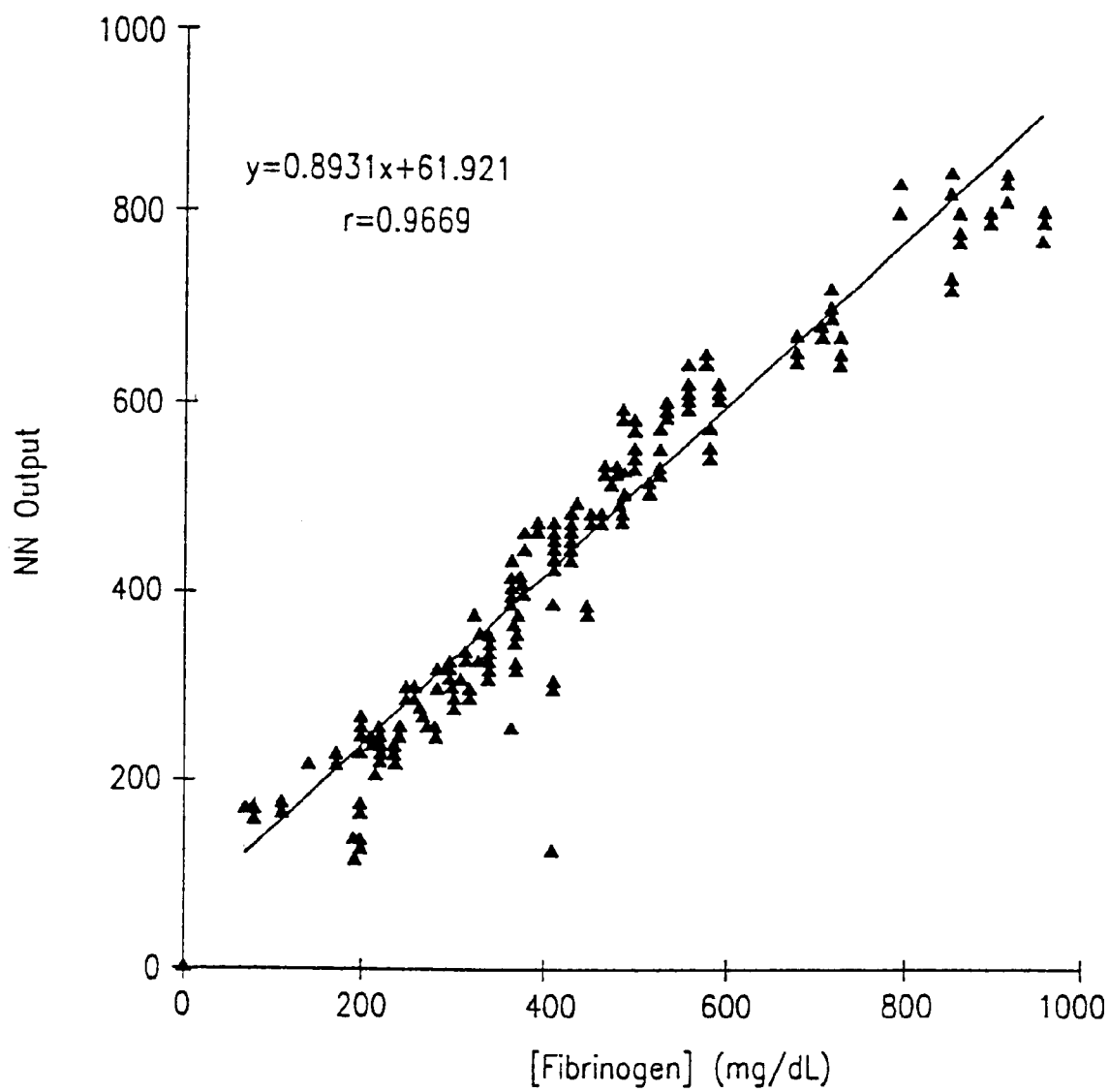
FIG. 26 shows the correlation between neural network output and measured fibrinogen concentration for cross-validation data set from neural networks trained to estimate fibrinogen concentration.
Figure 27:
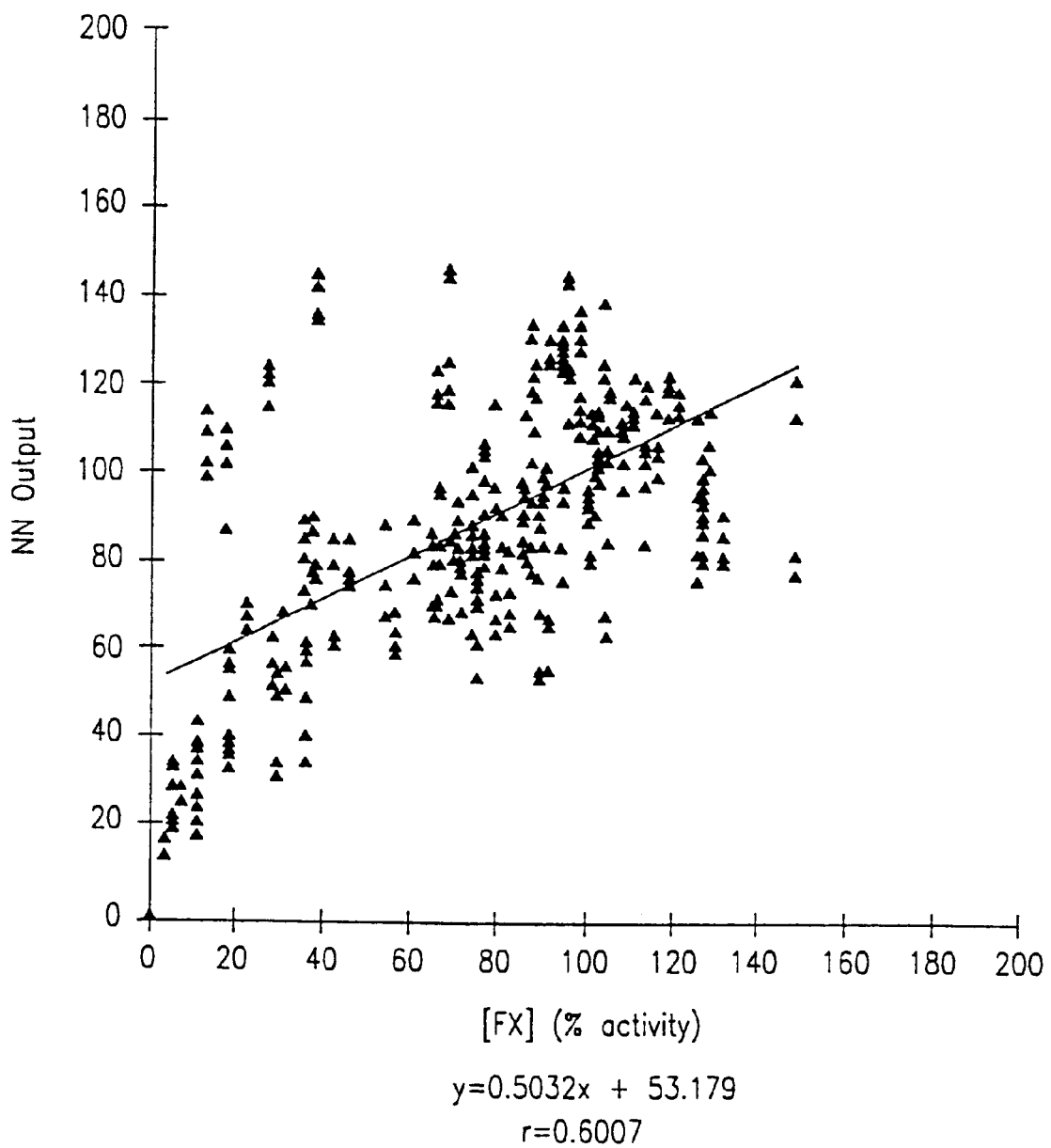
FIG. 27 shows the correlation between neural network output and measured FX concentration for cross-validation data set from neural networks trained to estimate FX concentration.

Neural networks were also trained to estimate actual protein concentrations (as opposed to a positive/negative classification at a defined cut-off) for FII, FV, FVII, FVIII, FIX, FX, FXI, FXII and fibrinogen. Linear correlation coefficients for the estimated and measured concentrations are shown in FIG. 25 for all experiments, and plots of the correlation data are shown in FIG. 26 for fibrinogen and FIG. 27 for FX. Correlation data between PT and APTT clot time and measured concentrations are also shown in FIG. 25 for comparison.

EXAMPLE

Self-Organizing Feature Maps

Neural networks using self-organizing feature maps and learning vector quantization were used to analyze optical data from clinical coagulation tests. Self-organizing feature maps using an unsupervised learning algorithm were trained with data from normal donors, patients with abnormal levels of coagulation proteins and patients undergoing anticoagulant therapy. Specimen categories were distinguishable in these maps with varying levels of resolution. A supervised neural network method, learning vector quantization, was used to train maps to classify coagulation data. These networks showed sensitivity greater than 0.6 and specificity greater than 0.85 for detection of several factor deficiencies and heparin.

An alternative approach to analyzing PT and APTT data with artificial neural networks (as set forth in Example 1) is by using self-organizing feature maps. Self-organizing feature maps contain layers of input and output neurons only and contain no hidden layers. Training is based on competitive learning where the output neurons compete with one another to be activated and only one output neuron is activated for any given set of inputs. Output neurons become selectively tuned to certain input patterns, and data with similar features tend to be grouped together spatially. This type of neural network may use either an unsupervised or supervised learning algorithm. When an unsupervised method is used, such as the self-organizing map (SOM) algorithm, unidentified input patterns are presented to the network during training and the output for each input pattern is the coordinates of the winning neuron in the output layer, or map. When a supervised method is used, such as learning vector quantization (LVQ), input patterns are presented along with a known sample classification to the network during training and the output is a unique predicted classification. The LVQ method is similar to SOM, except that the map is divided into classes, and the algorithm attempts to move outputs away from the boundaries between these classes.

MDA Simplastin L (PT reagent), MDA Platelin L (APTT reagent) and other reagents were obtained from Organon Teknika Corporation, Durham, N.C. 27712, USA, unless otherwise indicated. Factor-deficient plasmas for factor assays were obtained from Organon Teknika and George King Bio-Medical Corporation, Overland Park, Kans. 66210, USA. Additional factor-deficient plasmas were obtained from HRF, Raleigh, N.C. 27612, USA. Random samples, specimens from patients receiving heparin or oral anticoagulant therapy, and other specimens were obtained from Duke University Medical Center Coagulation Laboratory.

All testing was performed on MDA 180 coagulation analyzers (Organon Teknika). Optical measurements for PT and APTT assays were performed at a wavelength of 580 nm. Plasma specimens (n=200) included normal patients, patients with a variety of deficiencies, and patients undergoing heparin or other anticoagulant therapy. Duplicate PT and APTT assays were performed on each specimen using two MDA 180s to give a total of approximately 800 parameter sets from the 200 specimens. The total number varied slightly because of missing data due to insufficient sample, mechanical failure or unspecified failures. These specimens were also tested to determine the concentration of coagulation factors (FII, FV, FVII, FVIII, FIX, FX, FXI, FXII) heparin, and fibrinogen. The diagnostic cut-off for defining factor deficiencies was set at 30%; that is, specimens with a measured concentration of less that 30% of normal for a specific factor were defined as deficient and those with greater than 30% activity were defined as non-deficient. Samples were defined as positive for heparin if the measured heparin concentration was greater than 0.05 IU/ml.

Optical Data Processing

Optical profile data files were exported from MDA 180s and processed off-line. A set of nine parameters was derived to describe the timing, rate and magnitude of coagulation events for PT and APTT tests, as described previously. In this approach, the optical data for a PT or APTT assay was divided into three segments (a pre-coagulation segment, a coagulation segment and a post-coagulation segment) using divisions based on the minimum and maximum value of the second derivative for changes in optical signal with respect to time. Parameters included: 1) the times at which the onset, midpoint and end of the coagulation phase occur; 2) mean slopes for the pre-coagulation phase and the post-coagulation phase and the slope at the mid-point of coagulation; 3) terms for coagulation "acceleration" and "deceleration"; and 4) the magnitude of signal change during coagulation.

Self-Organizing Map Algorithm

A self-organizing feature map neural network consists of input and output layers of neurons. The self-organizing map (SOM) algorithm transforms an input vector (a set of data parameters from PT or APTT optical data for a single test) to an individual output neuron whose location in the output layer, or map, corresponds to features of the input data. These features tend to be spatially correlated in the map. There are five steps in the SOM learning process:

1. Unique weight vectors $w_j(0)$, are randomly chosen.
2. A sample from the training set is selected.
3. The best-matching winning neuron $i(x)$ at time n, using the minimum-distance Euclidean criterion $$i(x) = \arg\min_j\{\|x(n) - w_j(n)\|\}$$

is identified.
4. The weight vectors of all neurons are updated with the formula $$w_j(n+1) = \begin{cases} w_j(n) + \alpha(n)[x(n) - w_j(n)], & j \in N_c(n) \\ w_j(n), & j \notin N_c(n) \end{cases}$$

where $\alpha(n)$ is the learning rate parameter, and $N_c(n)$ is the neighborhood function centered around the winning neuron $i(x)$; both $\alpha(n)$ and $N_c(n)$ vary dynamically during training.
5. Steps 2 through 4 are repeated until the map reaches equilibrium.

The SOM tests were performed using the Self-Organizing Map Program Package (SOM_PAK) available from the Helsinki University of Technology, Laboratory of Computer Sciences. Two different sets of parameters were used as input to the SOMs: (1) the nine parameters from a PT assay, and (2) the nine parameters from the APTT assay. All data sets (786) were used to train the SOMs. A 10×10 map was trained using a hexagonal neighborhood in two stages. In the first stage, the map was trained for 1000 epochs (an epoch is one cycle through all data sets) with an initial learning rate parameter of 0.5 (decreasing linearly to zero during training) and a neighborhood radius of 10 (decreasing linearly to 1 during training). In the second stage, the map was trained for 10000 epochs using a learning rate parameter of 0.1 and a radius of 3.

Learning Vector Quantization

Learning vector quantization (LVQ) is a supervised learning algorithm often used to fine-tune self-organizing feature maps in order to use them in the role of a pattern classifier. The classification accuracy of the map is improved by pulling the weight vectors away from the decision surfaces that demarcate the class borders in the topological map. There are several variations of the LVQ algorithm; the one used here is referred to as LVQ1. The learning process is similar to the SOM algorithm described above, except that known sample classifications are included when weight vectors are updated (step 4):
1. Initial weight vectors $w_j(0)$, are randomly chosen.
2. A sample from the training set with a known classification is selected.
3. The best-matching winning neuron $i(x)$ at time n, using the minimum-distance Euclidean criterion $$i(x) = \arg\min_j\{\|x(n) - w_j(n)\|\}$$

is identified.
4. The weight vectors of all neurons are updated with the formula $$w_j(n+1) = \begin{cases} w_j(n) + \alpha(n)[x(n) - w_j(n)], & j = i, C_{w_i} = C_x \\ w_j(n) - \alpha(n)[x(n) - w_j(n)], & j = i, C_{w_i} \neq C_x \\ w_j(n), & j \neq i \end{cases}$$

where $C_{w_i}$ is the class associated with the vector $W_i$ and $C_x$ is the class associated with the input vector x.
5. Steps 2 through 4 are repeated until the map reaches equilibrium.

The LVQ tests were performed using the Learning Vector Quantization Program Package (LVQ_PAK), also available from the Helsinki University of Technology, Laboratory of Computer Sciences. The sets of parameters from the APTT assay or PT assays were used for the LVQ networks. The data parameter sets were divided evenly into training and cross-validation sets randomly by specimen, where all replicates for a given specimen were grouped either in the cross-validation set or training set. The same training and cross-validation sets were used throughout this study. The LVQ networks were trained to classify plasma samples into two categories, positive (factor-deficient specimens or specimens from patients undergoing anticoagulant therapy) and negative (non-deficient or no anticoagulant therapy), and results were compared to classification based on the measured factor concentration or therapeutic condition for the specimens. LVQ training was performed using 200 weight vectors, 10000 epochs, initial learning rate parameter of 0.5 (decreasing linearly to 0), and 7 neighbors used in knn-classification.

LVQ networks were evaluated using sensitivity (the proportion of known positive specimens that were correctly classified as positive by the network), specificity (the proportion of known negative specimens that were correctly classified as negative by the network), positive predictive value (PPV), negative predictive value (NPV) and efficiency. These terms are defined below, where TP, TN, FP and FN correspond to true positive, true negative, false positive and false negative classifications, respectively.

$$\text{sensitivity} = \frac{TP}{TP + FN}$$

$$\text{specificity} = \frac{TN}{FP + TN}$$

$$PPV = \frac{TP}{TP + FP}$$

$$NPV = \frac{TN}{TN + FN}$$

$$\text{efficiency} = \frac{TN + TP}{TP + FP + FN + TN}$$

Self-Organizing Map Algorithm

Self-organizing feature maps were trained using optical data parameters from either PT or APTT data for 200 specimens as input. Network output consisted of map coordinates f or each specimen. Contour plots were constructed for six categories of known specimen classifications: normal donors, specimens with heparin >0.05 IU/ml, fibrinogen >600 mg/dl, fibrinogen <200 mg/dl, patients receiving oral anticoagulants, and factor-deficient specimens (specimens with <30% of normal activity for FII, FV, FVII, FVIII, FIX, FX, FXI, or FXII). These contour plots depict the distribution of specimens within a category according to their map coordinates.

Figure 28:
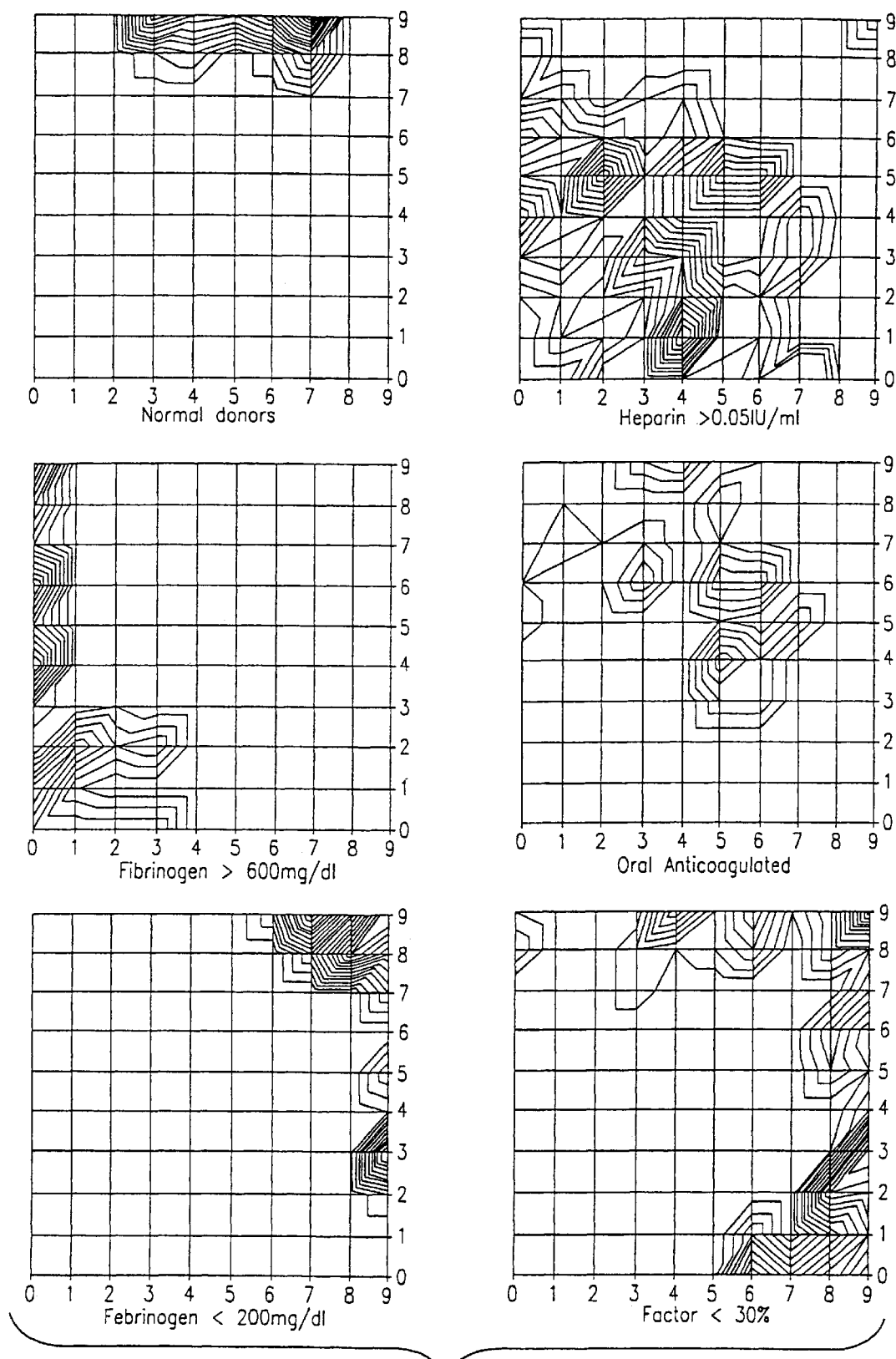
FIG. 28 shows SOM contour plots derived from APTT optical data for the six specimen categories.

FIG. 28: Contour plots for populations of samples used in training a self-organizing feature map using the unsupervised training method SOM based on data from APTT assays. Optical data parameters from 765 APTT assays were used to train this self-organizing feature map. The shaded areas represent the distribution of output neurons for specific specimen populations within the feature map. Each contour line represents an incremental step of one test result located at a given set of map coordinates.

FIG. 28 shows SOM contour plots derived from APTT optical data for the six specimen categories. Specimens containing low fibrinogen and high fibrinogen were classified at opposite borders of the SOM with no overlap. Normal populations showed some overlapping with low fibrinogen, factor deficient and oral anticoagulated categories. Overlap between normal specimens and edges of the high and low fibrinogen populations is expected, since some proportion of healthy donors have fibrinogen levels that are lower or higher than normal. Overlap between mapping of normal specimens and factor-deficient plasmas is also not surprising, since APTT tests are sensitive to some factor-deficiencies (but not others), whereas PT assays are sensitive to a separate subset of factor deficiencies. The low fibrinogen category tended to overlap the factor-deficient category, consistent with our observation that many factor-deficient specimens also had reduced fibrinogen levels. The heparin category tended to overlap the high fibrinogen category, again consistent with measured levels of fibrinogen for these specimens. Little or no overlap was observed between normal specimens and specimens containing heparin. Specimens from patients receiving oral anticoagulant therapy show significant overlap with both normal and heparin populations. This is consistent with known properties of APTT assays, which are sensitive to heparin therapy but relatively insensitive to oral anticoagulant therapy.

Figure 29:
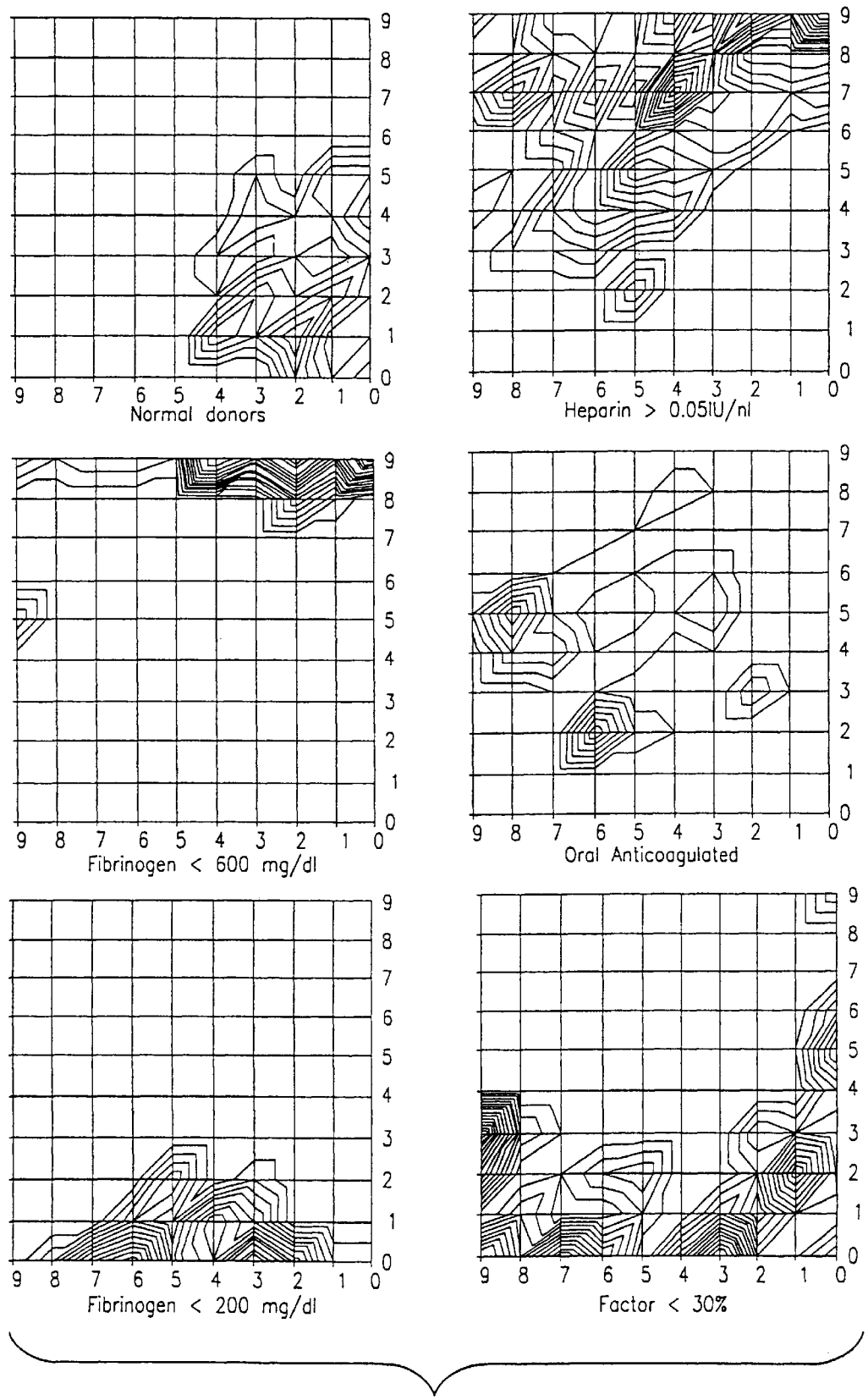
FIG. 29 shows contour plots for self-organizing feature maps trained with PT data.

FIG. 29: Contour plots for populations of samples used in training a self-organizing feature map using the unsupervised training method SOM based on optical data from 765 PT assays. Experimental details are as described in the Materials and Methods section and in FIG. 28.

Contour plots for self-organizing feature maps trained with PT data are shown in FIG. 29. Results are similar to maps from APTT data in several respects: (1) high and low fibrinogen were well resolved at opposite sides of the map; (2) normal specimens were localized in a region that overlapped low fibrinogen specimens slightly; (3) factor-deficient specimens were distributed between non-overlapping regions and regions that overlapped low fibrinogen and normal populations. Overlap was consistent with measured fibrinogen for some specimens, and with poor sensitivity of PT reagents to some factor deficiencies in other cases; (4) oral anticoagulated specimens showed some overlap with both normal and heparin populations; and (5) the heparinized population was distributed over a large portion of the map. Overlap between heparinized specimens and high fibrinogen populations was consistent with measured fibrinogen levels. The resolution of the heparin population is somewhat surprising, considering that PT reagents are relatively insensitive to heparin.

These results indicate that self-organizing feature maps are capable of distinguishing differences in optical data parameters from APTT and PT assays even when no information regarding specimen diagnosis is presented to the neural network. Resolution of specimen populations was variable, depending on reagent properties and sensitivities, and on whether specimens belonged to a given category uniquely or to multiple overlapping categories.

Learning Vector Quantization

Eighteen LVQ networks were trained to predict the presence or absence of a specific factor deficiency or therapeutic condition from APTT or PT optical data. Results for the cross-validation data are summarized in FIG. 30. Previous studies concluded that back-propagation neural networks were capable of sensitivity >0.6 while maintaining specificity >0.9 for all factors except FVII using an appropriate choice of PT and APTT data separately or in combination. In this study, LVQ networks using APTT data gave sensitivity >0.6 with specificity >0.85 for factors II, X, XI, and XII, and heparin. LVQ networks using PT data were able to achieve >0.6 sensitivity while maintaining >0.85 specificity for Factors II, X, and XI, and heparin (FIG. 30). Results from LVQ networks showed less sensitivity for prediction of FVII deficiencies, consistent with results from back-propagation networks. For FV, FVIII and FIX, sensitivity for predicting deficiencies from LVQ cross-validation sets was generally less (<0.35) than for factors II, X, XI and XII.

It is to be understood that the invention described and illustrated herein is to be taken as a preferred example of the same, and that various changes in the method and apparatus of the invention may be resorted to, without departing from the spirit of the invention or scope of the claims.

We claim:

1. A method for predicting the presence of at least one congenital or acquired imbalance or therapeutic condition associated with thrombosis or hemostasis from at least one time-dependent measurement profile, comprising:

(a) adding one or more reagents to a sample to cause coagulation in said sample and performing at least one time-dependent measurement on said sample by taking a plurality of measurements of a property of said sample over time, which property changes when said sample undergoes coagulation. so as to derive a respective at least one time-dependent measurement profile;

(b) defining a set of predictor variables which define the at least onetime-dependent measurement profile, said set of predictor variables including at least (i) rate or (ii) acceleration of fibrin polymerization;

(c) deriving a model that represents the relationship between the at least one congenital or acquired imbalance or therapeutic condition associated with thrombosis or hemostasis, and the set of predictor variables; and (d) utilizing the model of step (c) to predict the presence of the at least one congenital or acquired imbalance or therapeutic condition associated with thrombosis or hemostasis in the sample.

2. A method according to claim 1, wherein said set of predictor variables includes both rate and acceleration of fibrin polymerization.

3. The method of claim 1, wherein the rate is defined as the minimum of the first derivative of the at least one time-dependent measurement profile.

4. The method of claim 1, wherein acceleration is defined as the minimum of the second derivative of the at least one time-dependent measurement profile.

* * * * *

UNITED STATES PATENT AND TRADEMARK OFFICE
CERTIFICATE OF CORRECTION

PATENT NO. : 6,564,153 B2
DATED : May 13, 2003
INVENTOR(S) : Braun et al.

It is certified that error appears in the above-identified patent and that said Letters Patent is hereby corrected as shown below:

Title page,
Item [56], References Cited, OTHER PUBLICATIONS, please insert the following:

*3 x 15 Test Kit for Detection of Plasma Protein C Activity Using a Clotting End-Point*, Product # ACC-45, American Diagnostica Inc., 1-2 (Feb. 1989).

Artherotech, *VAP/CAD Lipoprotein Risk Assessment Tes and Sample of VAP Profile*, http://www.artherotech.com/risk_assesment.html Astion, et al., *Overtraining in neural networks that interpret clinical data*, Clin.Chem., 39(9):1998-2004 (1993).

Astion, et al., *The application of backpropagation neural networks to problems in pathology and laboratory medicine*, Arch. Pathol. Lab. Med., 116:995-1001 (Oct. 1992).

Baum and Haussler, *What size net gives valid generalization?*, Neural Computation, pg 81-89 (Jan. 1989)

Baumann, et al., *Computerized analysis of the in vitro activation of the plasmatic clotting system*, Haemostasis, 19:309-321 (1989).

Bluestein and Archer, *The sensitivity, specificity and predictive value of diagnostic information: a guide for clinicians*, Nurse Practitioner, 16(7):39-45 (July 1991).

Boone et al., *Neural networks in radiologic diagnosis*, Investigative Radiology, 25(9):1013-1023 (Sept. 1990).

Brandt, et al., *Effect of lupus anticoagulants on the activated partial thromboplastin time. Results of the College of American Pathologists survey program*, Arch.Pathol.Lab Med., 115:109-114 (Feb. 1991).

Braun et al., *Examination of prothrombin time (PT) and activated partial thromboplastin time (APTT) optical clot profiles using an automated thromobosis-hemostasis*, Coagulation Methods Instrumentation and Quality Control, pg 1236, Abstract #1286 (1995).

Braun, et al., *Properties of optical data from activated partial thromboplastin time and prothrombin time assays*, Thromb.Haemost., 78:1079-1087 (1997).

Cabana, et al., *Effects of the acute phase response on the concentration and density distribution of plasma lipids and apolipoproteins*, J.Lipid Res., 30:39-49 (1989).

Cabana, et al., *Inflammation-induced changes in rabbit CRP and plasma lipoproteins*, J.Immunol., 130(4):1736-1742 (April 1983).

UNITED STATES PATENT AND TRADEMARK OFFICE
CERTIFICATE OF CORRECTION

PATENT NO. : 6,564,153 B2
DATED : May 13, 2003
INVENTOR(S) : Braun et al.

Page 2 of 6

It is certified that error appears in the above-identified patent and that said Letters Patent is hereby corrected as shown below:

Title page (cont'd),

Cabana, et al., *Interaction of very low density lipoproteins (VLDL) with rabbit C-reactive protein*, J.Immunol., 128(5):2342-2348 (May 1982).

Canivet, et al., *Postoperative changes in lipid profile: their relations with inflammatory markers and endocrine mediators*, Acta Anaesthesiol.Belg., 40(4):263-268 (1989).

Carrol, et al., *Ortho Educational Monograph,The Clot Signature and New Aspects in Coagulation Testing*, Ortho Diagnostic Systems, Inc., pg. 1-20 (1989).

Christner and Mortensen, *Specificity of the binding interaction between human serum amyloid P-component and immobilized human C-reactive protein*, J.Biol.Chem., 269(13):9760-9766 (April 1994).

Dassen, et al., *Self-learning neural networks in electrocardiography*, J.Electrocardiol., 23 Suppl:200-202 (1990).

de Beer, et al., *Low density lipoprotein and very low density lipoprotein are selectively bound by aggregated C-reactive protein*, J.Exp.Med., 156:230-242 (July 1982).

Dennis et al., *Utility of prothrombin time waveform analysis in the routine clinical setting*, Abstract Instruction and Submission Form, (Sept. 1999).

Downey et al., *The robustness and reproducibility of APTT waveform analysis in relation to reagent and batch variation*, abstract only.

Downey et al., *Transmittance waveforms - adjunctive information from automated coagulometers*, Int.J.Hematol., 64 Suppl:S160, Abstract #619, (Aug. 1996).

Downey, et al., *Novel and diagnostically applicable information from optical waveform analysis of blood coagulation in disseminated intravascular coagulation*, Br.J.Haematol., 98:68-73 (1997).

Downey et al., *Early Identification and Prognostic Implications in Disseminated Intravascular Coagulation through Transmittance Waveform Analysis*, Thromb. Haemost 1998; 80: 65-9.

Engler, R., *[Acute-phase proteins in inflammation]*, C.R.Seances Soc.Biol.Fil., 189(4):563-578 (1995).

Furlong, et al., *Neural network analysis of serial cardiac enzyme data. A clinical application of artificial machine intelligence*, Am.J.Clin.Pathol., 96(1):134-141 (July 1991).

Gewurz, et al., *C-reactive protein and the acute phase response*, Adv.Intern.Med., 27:345-372 (1982).

Givens and Braun, *Classification of factor deficiencies from coagulation assays using neural networks*, Int.J.Med.Inf., 46:129-143 (1997).

Givens et al., *Interpretation of clot formation parameters from APTT and PT assays using neural networks*, Clin.Chem., 42(6):S192, Abstract #399 (1996).

Givens, et al., *Predicting the presence of plasma heparin using neural networks to analyze coagulation screening assay optical profiles*, Comput.Biol.Med., 26(6):463-476 (1996).

Givens, T.B., *Clot signatures*, Clin.Hemostasis Rev., pg 11-12 (Aug. 1997).

Harris et al., *Reactivity of serum amyloid P component with C-reactive protein and IgM*, Clin.Res., 37, Abstract #614A (1989).

UNITED STATES PATENT AND TRADEMARK OFFICE
CERTIFICATE OF CORRECTION

PATENT NO. : 6,564,153 B2
DATED : May 13, 2003
INVENTOR(S) : Braun et al.

It is certified that error appears in the above-identified patent and that said Letters Patent is hereby corrected as shown below:

Title page (cont'd),

Heuck and Baumann, *Kinetic analysis of the clotting system in the presence of heparin and depolymerized heparin*, Haemostasis, 21:10-18 (1991).

Hoffman and Callahan, *The Coag-A-Mate RA4 Fibrinogen Assay*, Interface (Organon Teknika), pg 3-7 (1990).

Hulman and Fuller, *Comparison of fat agglutination slide test and latex test for C- reactive protein*, Clin.Chim.Acta, 165:89-93 (5-29-1987).

Hulman, et al., *Agglutination of intralipid by sera of acutely ill patients*, Lancet, 2:1426-1427 (Dec. 1982).

Hulman, G., *The pathogenesis of fat embolism*, J.Pathol., 176:3-9 (1995).

Husebekk, et al., *High-density lipoprotein has different binding capacity for different apoproteins. The amyloidogenic apoproteins are easier to displace from high-density lipoprotein*, Scand.J.Immunol., 28:653-658 (1988).

Koagulab 16-S Plus Graphics, Koagulab 32-S Coagulation System, Graphics Binder, 2,3,5,6,8-12, 14-17,19-21,23.

Khanin and Semenov, *A mathematical model of the kinetics of blood coagulation*, J.Theor.Biol., 136:127-134 (Jan. 1989).

Lagrand, et al., *C-reactive protein as a cardiovascular risk factor: more than an epiphenomenon?*, Circulation, 100:96-102 (July 1999).

Lindh, et al., *Agglutinate formation in serum samples mixed with intravenous fat emulsions*, Crit Care Med., 13(3):151-154 (March 1985).

Malle, et al., *Serum amyloid A (SAA): an acute phase protein and apolipoprotein*, Atherosclerosis, 102:131-146 (1993).

McCarty, M., *Historical perspective on C-reactive protein*, Ann.N.Y.Acad.Sci., 389:1-10 (1982).

McDonald, et al., *A monoclonal antibody sandwich immunoassay for serum amyloid A (SAA) protein*, J.Immunol.Methods, 144:149-155 (11-22-1991).

*Package insert for Ortho Brain Thromboplastic Reagent*, Ortho Diagnostic System, Inc., pg. 1-7 (Oct. 1985).

Pattichis, et al., *Efficient training of neural network models in classification of electromyographic data*, Med.Biol.Eng Comput., 33(3):499-503 (May 1995).

Pepys, et al., *C-reactive protein: binding to lipids and lipoproteins*, Int.Rev.Exp.Pathol., 27:83-111 (1985).

Pohl, et al., *The quick machine—a mathematical model for the extrinsic activation of coagulation*, Haemostasis, 24:325-337 (1994).

Richter, et al., *The fat emulsion agglutination test: a reliable and cost effective alternative to the latex agglutination test for rapid bedside CRP measurement*, Clin.Chim.Acta, 261:141-148 (May 1997).

Robin et al., *Prognostic value of waveform analysis in the intensive care setting*, Intensive Care Med., 25(Suppl 1):S63 (1999).

Rowe, et al., *Agglutination of intravenous lipid emulsion ('Intralipid') and plasma lipoproteins by C-reactive protein*, Clin.Exp.Immunol., 66:241-247 (1986).

Rowe, et al., *Circulating human C-reactive protein binds very low density lipoproteins*, Clin.Exp.Immunol., 58:237-244 (1984).

UNITED STATES PATENT AND TRADEMARK OFFICE
CERTIFICATE OF CORRECTION

PATENT NO. : 6,564,153 B2
DATED : May 13, 2003
INVENTOR(S) : Braun et al.

It is certified that error appears in the above-identified patent and that said Letters Patent is hereby corrected as shown below:

Title page (cont'd),

Rowe, et al., *In vivo turnover studies of C-reactive protein and lipoproteins in the rabbit*, Clin.Exp.Immunol., 58:245-252 (1984).

Rowe, et al., *Rabbit and rat C-reactive proteins bind apolipoprotein B-containing lipoproteins*, J.Exp.Med., 159:604-616 (Feb. 1984).

Sabbatini, R.M.E., *Neural networks for classification and pattern recognition of biological samples*, Conf.of the Engineering in Medicine and Biology Society (IEEE, New York, U.S.) 15:265-266 (Oct. 1983).

Sammalkorpi, et al., *Lipoproteins and acute phase response during acute infection. Interrelationships between C-reactive protein and serum amyloid-A protein and lipoproteins*, Ann.Med., 22:397-401 (1990).

Schwalbe, et al., *Association of rat C-reactive protein and other pentraxins with rat lipoproteins containing apolipoproteins E and A1*, Biochemistry, 34(33):10432-10439 (Aug. 1995).

Schweiger, et al., *Evaluation of laboratory data by conventional statistics and by three types of neural networks*, Clin.Chem., 39(9):1966-1971 (1993).

Simmons, A. *Ethanol-gel solubility test*, In: Technical Hematology, 3rd Edition, J.B. Lippincott Company, Philadelphia, PA, pg. 334-335 (1980).

Stewart, et al., *Sensitive and rapid measurement of C-reactive protein (CRP) by lipid agglutination*, J.Clin.Pathol., 40:585-588 (1987).

Swanson, et al., *Human serum amyloid P-component (SAP) selectively binds to immobilized or bound forms of C-reactive protein (CRP)*, Biochim.Biophys.Acta, 1160:309-316 (12-28-1992).

Sweeney et al., *Abnormal clot signatures in hereditary bleeding disorders*, Blood, 74 Suppl 1(7):395, Abstract #1509 (Nov. 1989).

Sweeney et al., *Abnormal clot signatures in hereditary bleeding disorders*, The American Society of Hematology Abstract Reproduction Form (1989).

Sweeney et al., *Kinetic clot parameters in gynecological tumors*, Blood, 76 Suppl 1(10):439a, Abstract #1745-(Nov. 1990).

Swets, J. A., *Measuring the accuracy of diagnostic systems*, Science, 240:1285-1293 (June 1988).

Talstad, I., *Which coagulation factors interfere with the one-stage prothrombin time?*, Haemostasis, 23:19-25 (1993).

Toh and Downey, *A previously unrecognized mechanism that is calcium-dependent and thrombin-independent characterizes the pre-DIC state*, The American Society of Hematology, 1999 Submission Form, Abstract #450426 (1999).

Toh and Downey, *The mechanism underlying the atypical clot waveform profile of DIC is thrombin-independent but calcium-dependent*, European Haematology Association, Abstract Form (June 2000).

Toh et al., *APTT Waveform analysis: predicting mortality in the critical care setting using the light transmittance level at 18 seconds*, XVII Congress International Society for Thrombosis & Haemostasis, Abstract Submission Form, (Aug. 1999).

Toh et al., *Characterization of the novel calcium-activation, thrombin suppression assay (CaTs) in the DIC of sepsis*, abstract only.

Toh et al., *Impending clinical decompensation is characterized by the detection of a novel calcium-dependent and thrombin-independent pathway*, 5th World Congress on Trauma, Shock, Inflammation and Sepsis -- Pathophysiology, Immune Consequences and Therapy, Abstract Submission Form, (Feb. 2000).

UNITED STATES PATENT AND TRADEMARK OFFICE
CERTIFICATE OF CORRECTION

PATENT NO.    : 6,564,153 B2
DATED         : May 13, 2003
INVENTOR(S)   : Braun et al.

It is certified that error appears in the above-identified patent and that said Letters Patent is hereby corrected as shown below:

Title page (cont'd),

Toh et al., *Prospective detection of pre-disseminated intravascular coagulation (DIC) in a sepsis cohort by waveform analysis*, XVII Congress International Society for Thrombosis & Haemostasis, Abstract Submission Form, (Aug. 1999).

Toh et al., *Waveform analysis of the prothrombin time (PT) assay also shows characteristic changes in disseminated intravascular coagulation*, XVII Congress International Society for Thrombosis & Haemostasis, Abstract Submission Form, (Aug. 1999)

Toh, C.H., *Disseminated intravascular coagulation (DIC): Old problem, new hope*, Clin.Hemostasis Rev., pg 18 (Jan. 1998).

Triplett, et al., *Graphic monitoring of coagulation assays*, American Clinical Laboratory, pg 1-5 (April 1989).

Wilkins, et al., *Rapid automated enzyme immunoassay of serum amyloid A*, Clin.Chem., 40(7):1284-1290 (1994).

Zweig and Campbell, *Receiver-operating characteristic (ROC) plots: a fundamental evaluation tool in clinical medicine*, Clin.Chem., 39(4):561-577 (1993).

*Ortho Factor VIII: C Deficient Plasma*, Ortho Diagnostic Systems, Inc., pp. 1-2 (September 1998)

C. Downey, et al. *Br. J. Haematol.*, 136: 18854 (1997)

Preciado-Pratt et al. *Serum Amyloid A Complexed with Extracellular Matrix Induces the Secretion of Tumor Necrosis Factor-alpha by Human T-lymphocytes*, Letters in Peptide Science, vol. 5, (1998), no. 5-6, pl 349-55 (abstract only).

Eitoku et al." Studies on the Serum Amyloid A (SAA): Part 2 Latex Agglutination Nephelometric Immunoassay System for Quantitation of SAA in Human Serum and its Clinical Values," *Physico Chem. Biol.*, 37: 19-23 (Feb. 1993).

Rybarska et al. "The Detective of Specific Acute Phase Serum Protein Complexes and Immune Complexes by Congo Red Binding," *Journal of Physiology and Pharmacology*, 1995, vol. 46 (2), pp. 221-31 (abstract only).

Maury, C.P.J. "Clinical Usefulness of Serum Amyloid A and C-reactive Protein Measurements in Inflammatory Disorders a Comparative Study," *Marker Proteins in Inflammation Proceedings*, vol. 3, Symposium, Lyon, France, June 1985 (abstract only).

Baumann et al., "Simulation of the extrinsic pathway of the plasmatic clotting system," *Haemostasis*, 21:329-337 (1991).

Zuckerman et al. "Comparison of thrombelastography with common coagulation tests," *Thromb Haemostas*, 46: 752-6 (1981).

"The Clot Signature and New Aspects in Coagulation Testing," *Ortho Diagnostic Systems, Inc.*, 1-20 (Aug. 1989).

UNITED STATES PATENT AND TRADEMARK OFFICE
CERTIFICATE OF CORRECTION

PATENT NO. : 6,564,153 B2
DATED : May 13, 2003
INVENTOR(S) : Braun et al.

It is certified that error appears in the above-identified patent and that said Letters Patent is hereby corrected as shown below:

Column 1,
Line 5, insert -- RELATED APPLICATIONS --
Line 11, should read -- continuation-in-part of U.S. application Ser. No. 08/859,773 --

Column 2,
Line 13, should read -- In Pohl et al. (1994), supra, a dynamic model of the --
Line 16, should read -- partial thromboplastin time (APTT), thrombin time (TT), --
Line 51, should read -- The PT and APTT assays rely primarily upon measurement --

Column 6,
Line 8, should read -- Factors II, V, VII, VIII, IX, X, XI and XII, as well as ATIII --
Line 19, should read -- reaction within the sample. A property over time is auto- --

Column 7,
Line 1, should read -- buffer were obtained from Organon Teknika Corporation, --
Line 6, should read -- polypropylene tubes and stored at -80° until evaluated. 757 --

Column 9,
Line 23, should read -- The percent classification, φ, describes the percent of the --

Column 11,
Line 18, should read -- Optical measurements for APTT and PT assays were --

Column 20,
Line 32, should read -- sample undergoes coagulation, so as to derive a respective --
Line 35, should read -- at least one time-dependent measurement profile, said --

Signed and Sealed this

Twenty-second Day of March, 2005

JON W. DUDAS
*Director of the United States Patent and Trademark Office*